United States Patent
Cimochowski et al.

(10) Patent No.: US 6,398,734 B1
(45) Date of Patent: *Jun. 4, 2002

(54) ULTRASONIC SENSORS FOR MONITORING THE CONDITION OF FLOW THROUGH A CARDIAC VALVE

(75) Inventors: George E. Cimochowski, Dallas, PA (US); George W. Keilman, Woodinville, WA (US)

(73) Assignee: VascuSense, Inc., Woodinville, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/373,445

(22) Filed: Aug. 12, 1999

Related U.S. Application Data

(60) Continuation-in-part of application No. 09/078,818, filed on May 14, 1998, which is a division of application No. 08/949,413, filed on Oct. 14, 1997, now Pat. No. 5,807,258.

(51) Int. Cl.[7] .................................................. A61B 8/12
(52) U.S. Cl. ........................ 600/454; 600/459; 600/504; 623/2
(58) Field of Search ................................. 600/437, 439, 600/454–456, 459, 504; 623/222, 900

(56) References Cited

U.S. PATENT DOCUMENTS

| | | | |
|---|---|---|---|
| 3,661,146 A | * | 5/1972 | Peronneau et al. ......... 600/454 |
| 4,769,032 A | * | 9/1988 | Steinberg .................... 623/900 |
| 4,926,875 A | * | 5/1990 | Rabinovitz et al. ......... 600/459 |
| 5,284,146 A | * | 2/1994 | Czar et al. ................... 604/175 |
| 5,487,760 A | * | 1/1996 | Villafara ........................ 623/2 |
| 5,588,436 A | * | 12/1996 | Narayanan et al. ......... 600/459 |
| 5,967,989 A | * | 10/1999 | Cimochowski et al. ..... 600/459 |

* cited by examiner

Primary Examiner—Francis J. Jaworski
(74) Attorney, Agent, or Firm—Ronald M. Anderson

(57) ABSTRACT

A parameter indicative of the condition of a cardiac valve is determined by monitoring blood flow and/or velocity in a vessel that is coupled to the cardiac valve or in a chamber adjacent to an artificial cardiac valve. One or more ultrasonic transducers are provided either in a wall or a cuff disposed about a cardiac vessel to monitor the parameter in regard to a natural or artificial cardiac valve, or in a support sewing ring of an artificial cardiac valve. A conformal array transducer or a tilted element is used to monitor fluid flow or velocity based on the effect of the blood on ultrasonic waves produced by the transducers. The conformal array transducer comprises a plurality of elements that are excited with an input signal provided by an implantable electronics circuit, producing ultrasonic waves. Transit time or Doppler measurements are made using an appropriate number of these transducers to determine either blood volumetric flow or velocity. Various implantable electronic circuits are disclosed that enable a transducer to be driven and to receive an ultrasonic signal indicative of the status of blood flow and thus, the condition of the cardiac valve. A radio frequency (RF) coil is coupled to an external coil. The external coil is connected to a power supply and monitoring console, conveying power to the ultrasonic transducers and receiving data signals that enable the condition of the cardiac valve to be determined.

64 Claims, 11 Drawing Sheets

ULTRASONIC SENSORS FOR MONITORING THE CONDITION OF FLOW THROUGH A CARDIAC VALVE

RELATED APPLICATIONS

This application is a continuation-in-part application, based on prior application Ser. No. 09/078,818, filed on May 14, 1998, which in turn is a divisional of application Ser. No. 08/949,413, filed on Oct. 14, 1997 and issued as U.S. Pat. No. 5,807,258 on Sep. 15, 1998, the benefit of the filing dates of which is hereby claimed under 35 U.S.C. §120.

FIELD OF THE INVENTION

The present invention generally relates to the use of ultrasonic transducers to monitor flow and velocity, and more specifically, to the use of such sensors to monitor flow and velocity of blood through a cardiac valve, so as to determine the condition of the valve.

BACKGROUND OF THE INVENTION

A cardiac valve that is diseased or defective can be surgically excised and replaced with an artificial valve. Once the valve has been replaced, it will be desirable to carefully monitor the condition of the valve, to ensure that it continues to function properly. While it is possible to externally examine a patient and reach some nominal diagnosis concerning the condition of a replacement valve and its proper functionality, an external examination may fail to identify incipient problems. If the valve subsequently fails catastrophically, the patient may die before surgery can correct the problem. Imaging techniques and other diagnostic evaluations of the proper functioning of an artificial valve may be impractical, patent application particularly because of expense and because they require the patient to visit facilities where such evaluations can be carried out. Accordingly, it will be apparent that means for performing such an evaluation on a continuing basis while a patient remains mobile and continues to lead a normal daily routine that does not involve frequent visits to a medical facility would be very desirable.

Often, a patient's natural cardiac valve may be diseased, but still capable of functioning to at least a limited extent. Again, it would be helpful to monitor the condition of the natural cardiac valve on a continuous basis to enable surgery to be performed to replace the valve before the patient suffers a serious heart attack caused by a failure of the valve. Currently, the most effective technique to evaluate the condition of either an artificial cardiac valve or a natural valve is to monitor the flow of blood through the valve. However, there is no convenient way to accomplish this monitoring on a continuing basis. The velocity and volume of blood flowing through a cardiac valve are ideal parameters for determining whether the valve is functioning properly. Distal and proximal fluid pressure across a valve are a further indication of its condition.

Ideally, it would be desirable to employ means for monitoring the condition of fluid flow through a cardiac valve remotely, either continually or only periodically, upon demand. The means used for monitoring the condition of a cardiac valve should enable a physician to evaluate the parameters noted above at a remote location outside the patient's body, without resorting to an invasive procedure. Further, the monitoring means should at least periodically be supplied power from an external source, since it is unlikely that a battery could provide the power required by sensors and circuitry required to monitor flow and other parameters indicative of a condition of a cardiac valve for an extended period of time.

Various techniques are known in the prior art for monitoring flow and velocity of a fluid inside a blood vessel, but in each case, the devices employed for this purpose are intended for relatively short-term use immediately following surgery and are not acceptable for the extended period for monitoring fluid flow, as noted above. For example, one type of volume flow measurement system described in U.S. Pat. No. 4,227,407 uses two piezoelectric ultrasonic transducers that are alternately activated to produce ultrasonic waves. The ultrasonic waves pass into a vein or artery and are modified by the flow of blood in the vessel interposed between the two transducers. When one transducer is actively transmitting an ultrasonic wave, the other transducer serves as a receiver of the wave. The two transducers are oriented at an acute angle relative to the longitudinal axis of the blood vessel, so that the ultrasonic sound wave propagating through the blood vessel has a component in the direction (or opposite to the direction) of blood flow through the vessel. In an alternative embodiment disclosed in this patent, the transducers are located on the same side of the blood vessel, spaced apart along its longitudinal axis, and a reflective plate is disposed on the opposite side of the vessel, intermediate the positions of the two transducers. An ultrasonic wave transmitted from either transducer passes through the blood vessel, is reflected from the reflective plate, and is received by the other transducer. The difference in the transit times for the sound waves transmitted from the two transducers (in both embodiments) is indicative of the flow through the blood vessel. If transducers used only extend over a small portion of the diameter of the vessel, the difference in transit time would be indicative of the velocity of blood flowing in the blood vessel. However, since the transducers shown in this prior art reference are sufficiently large so that the diameter of the blood vessel is fully encompassed by the sound waves the transducers emit, the transit time is indicative of the flow of blood flowing through the vessel, i.e., volumetric flow. The flow is thus determined without any consideration of the internal cross-sectional area of the blood vessel. While this prior art apparatus is useful for monitoring blood flow (or velocity) through a blood vessel that is surgically exposed, the transducers are too large to be implanted within a patient's body and are unsuitable to monitor the fluid flow status through a blood vessel associated with a cardiac valve. Also, to provide a good acoustic path between the transducers and the adjacent surface of the vessel, it may well be necessary to apply the transducers against the surface of the vessel with sufficient force to distort the wall of the vessel into the notch in the apparatus that is formed adjacent the sloping face of each transducer. Such distortion of the vessel may adversely affect the accuracy of the measurements and is undesirable over an extended period of time.

Another prior art approach for determining the velocity and/or flow of blood in a vessel employs Doppler sensing using either a pulsed or continuous wave ultrasonic signal that is emitted at a defined angle relative to the longitudinal axis of the blood vessel. If only a single transducer is used, the angle must be accurately known, and any error in the angle must be corrected. However, if a transmitting transducer is disposed on one side of the blood vessel and a receiving transducer is disposed on the opposite side of the blood vessel, angled so that the ultrasonic beam reflected from the blood flowing through the vessel is directed to the receiving transducer, an angle correction is not required.

Examples of apparatus for Doppler monitoring of blood flow are disclosed in U.S. Pat. Nos. 5,289,821 and 5,588,436. In the first of these two patents, an ultrasonic transducer wire assembly is secured to a strip of biologically inert or absorbable material, which is wrapped around and in contact with a blood vessel to form a cuff, preferably disposed downstream from an anastomosis of the vessel, such as may be performed during microvascular surgery. The wire from the transducer exits the patient's body through a slit and is coupled to ultrasonic processing means that determine the velocity of blood flowing through the vessel by the Doppler processing of an ultrasonic wave that is transmitted by the transducer and received as a reflection from the blood in the vessel. After monitoring the velocity of blood flow for about three to seven days to determine if any thromboses has formed that would impede blood flow, the wire and transducer can be pulled from the strip and removed from the body through a small incision, leaving the strip behind. This device is not usable for an extended period of time (much beyond seven days), since the slit in the skin where the wires penetrate represents a pathway for infection. Further, the patent teaches that the invention is primarily intended for use on blood vessels close to the skin surface, such as those resulting from microvascular surgery on a patient's hand and thus would be unusable for monitoring the fluid flow through a blood vessel adjacent to the heart and deep within a patient's body.

In the second patent listed above, a Doppler scheme for determining blood velocity in a vessel is disclosed, wherein an elongate sheath is provided with a transducer head at its distal end. Two wires extend longitudinally through the sheath to a transducer that is mounted preferably at an angle of about 45° relative to the longitudinal axis of the sheath. A biocompatible material such as epoxy encases both the transducer and the distal ends of the wires. This molded housing for the transducer has a concave surface that fixes the transducer relative to the blood vessel and provides a close fit to the surface of the blood vessel to provide a path for ultrasonic sound waves produced by the transducer to enter the blood vessel and for reflected waves to be detected by the transducer. A mesh band is wrapped around the transducer, and its ends are sutured together to hold the concave surface of the material in contact with the outer surface of the blood vessel. The band is made of VICRYL™ mesh or other absorbable/inert material. A thread having ends that run inside and along the longitudinal axis of the sheath secure the band to the distal end of the sheath. The proximal end of the sheath is preferably left extending through the patient's skin after the device is installed to monitor blood velocity through a vessel in contact with the concave surface of the material at the distal end of the probe. After the measurements are concluded (purportedly, after a maximum of up to 21 days), the thread is cut and pulled from its engagement with the band, so that the transducer, wires, and sheath can be withdrawn, leaving the band in place—possibly to be absorbed, depending on the material from which the band is fabricated.

Each of the Doppler devices discussed above is used to monitor the velocity of blood through a vessel, and to the extent that the cross-sectional area of the vessel is assumed or known, the devices enable flow to be estimated. However, neither prior art Doppler device is intended to monitor flow or velocity of blood for more than a few days. In addition, the elongate sheath used with the latter device is relatively bulky and not suitable for installation where available space around the vessel is limited. Both devices put the patient at risk of infection, because at least the wires coupled to the transducer must extend from inside the patient's body through the skin, to an external monitoring system.

Another prior art technique for monitoring flow with a Doppler system that is more compact than the devices discussed above is based on a surface acoustic wave (SAW) transducer that couples a "leaky wave" into the wall of a blood vessel. The SAW transducer includes pairs of interdigital electrodes fabricated on a piezoelectric substrate that is relatively small, e.g., about 1.6 mm by 2.2 mm. This transducer is described in a paper entitled "Miniature Doppler Probe Using a Unidirectional SAW Transducer" by T. Matsunaka and S. Yamashita. To produce a unidirectional interdigital SAW transducer, the drive signal applied to half of the electrodes is phase shifted by 90° relative to that applied to the other electrodes. The ultrasonic waves produced by the device propagate primarily in only one direction at an angle, □, thereby enabling the direction of fluid flow in a blood vessel to be determined. The wave that would normally be transmitted in the opposite direction at an angle, –□□ is instead canceled by the interference between the interdigital electrodes driven with signals that are phase shifted relative to each other. This prior art reference states that the signal produced by a prototype SAW transducer had a maximum amplitude at a radiation angle of about 54.5°, with a beam width of about 2.5 times the actual electrode width (one mm) and suggests that the beam width might be reduced by modifying the electrode layout to achieve a "focusing effect."

Several advantages of the interdigital electrode SAW transducer design relative to the other devices available to measure flow and velocity of blood through a vessel to determine the condition of a cardiac valve are apparent. The interdigital SAW transducer is substantially smaller in size than the prior art devices and requires less energy to produce ultrasonic waves. Further, the beam width is substantially wider than the physical size of the electrodes so that the apparatus can be made relatively small compared to the size of the beam that it produces. In addition, unlike the single transducer apparatus shown in the prior art first discussed above, which produce both forward and rearwardly directed waves that are affected by the velocity of blood in either direction but cannot determine the direction of flow, the unidirectional SAW transducer is able to monitor fluid velocity and determine the direction of the fluid flow.

The prior art does not disclose an interdigital transducer that monitors transit time. Instead, each of the interdigital transducers of the prior art SAW transducer discussed above produces a leaky SAW wave and employs the Doppler effect to determine the velocity of blood in a vessel. For monitoring velocity and flow through a vessel and thereby determine the condition of a cardiac valve, it would be preferable to employ a transducer that is compact, like an interdigital SAW transducer, but one that also has the ability to measure transit time and thus flow, generally independent of any considerations of velocity profile or cross-sectional area of the vessel. This transducer should be implantable, preferably built into or secured to a supporting structure that is installed in a patient's body, supplied with electrical power from a source outside the patient's body, without using wires that penetrate the dermal layer, and should also permit monitoring of the flow, velocity, and pressure of a fluid without use of wires that pass through the skin. Currently, no compact prior art device is available that can remotely monitor flow and velocity parameters of a blood vessel to determine the condition of a cardiac valve for long periods (e.g., for months or even years) of time. Further, none of the prior art devices is designed to be wholly implanted, remotely monitored, and provided with power from a remote source outside the patient's body.

SUMMARY OF THE INVENTION

In accord with the present invention, a band is defined that is adapted to be applied around a cardiac vessel to monitor a condition of a cardiac valve that controls blood flow through the cardiac vessel in a patient's body. The band includes a biocompatible material that is sufficiently elastomeric to be wrapped around a cardiac vessel, forming a cuff. A first transducer is disposed within the wall of the cuff and produces a signal indicative of a parameter of the blood flowing through the cardiac vessel. This parameter is thus indicative of a condition of the cardiac valve. A coil is coupled to the first transducer and conveys the signal to a point external to the patient's body for use in evaluating a condition of the cardiac valve as a function of the parameter of the blood flowing through the cardiac vessel.

The first transducer preferably includes a plurality of elements formed on a piezoelectric substrate. When excited by a radio frequency signal, the elements emit ultrasonic waves that propagate into the cardiac vessel and are affected by the blood flowing through the cardiac vessel. A receiver of the ultrasonic waves produces the signal indicative of the parameter and is coupled to the coil so that the signal produced by the receiver is conveyed outside the patient's body.

The parameter is preferably either one of a velocity and a flow of the blood through the cardiac vessel, and the signal that is indicative of the parameter is determined as a function of the blood's effect on the ultrasonic waves within the cardiac vessel. It is also preferably that the receiver comprise a second transducer including a plurality of elements formed on a piezoelectric substrate. The second transducer is disposed within the wall of the cuff and responds to the effect of the blood in the cardiac vessel on the ultrasonic waves to produce the signal indicative of the parameter. The first transducer and the second transducer are preferably disposed on opposite sides of the cuff, so that the ultrasonic waves pass through the cardiac vessel when traveling between the two transducers. The signal produced by the second transducer provides an indication of a transit time of the ultrasonic waves through the cardiac vessel.

The plurality of elements comprising the first transducer and the second transducer are sufficiently flexible to conform to a curved shape of an exterior surface of a cardiac vessel. In addition, the plurality of elements comprising the first transducer are divided into a first portion and a second portion, with elements comprising the first portion interdigitally dispersed among elements comprising the second portion. The elements in the first portion are adapted to couple to the radio frequency signal in one polarity, and the elements comprising the second portion are adapted to couple to the radio frequency signal with an opposite polarity, so that the ultrasonic waves produced by the elements comprising the second portion are phase shifted by about 180° relative to the ultrasonic waves produced by the elements comprising the first portion.

Also preferably included in this embodiment is a phase shifter. The elements comprising the first transducer are then divided into four portions arranged in an ordered array in which each successive element is from a different one of the four portions, taken in order. The radio frequency signal is applied to the phase shifter, and a phase shifted signal produced by the phase shifter is applied to at least two of each successive four elements to provide about a 90° phase difference between the ultrasonic waves emitted by successive elements. Consequently, the ultrasonic waves that are emitted by the first transducer in one direction are substantially canceled due to a destructive interference.

In another embodiment, the first transducer and the second transducer are spaced apart from each other along a side of the cuff, and a reflector is disposed on an opposite side of the cuff from the first transducer and generally opposite a point between the first transducer and the second transducer. The ultrasonic waves from the first transducer then pass through the cardiac vessel and are reflected back toward the second transducer by the reflector.

The first transducer and the second transducer may alternately function as an emitter and as a receiver of the ultrasonic waves during successive time intervals. The radio frequency signal are coupled to the plurality of elements comprising the second transducer when it functions as the emitter, while the plurality of elements comprising the first transducer are then coupled to the coil and produce the signal indicative of the parameter in response to the ultrasonic waves affected by the blood in the cardiac vessel. Also included is a multiplexer that is used for alternately coupling the first and the second transducers to the radio frequency signal and to the coil.

The frequency of the radio frequency signal is preferably controlled to determine a beam angle along which the ultrasonic waves are emitted by the first transducer, in at least one of the embodiments. The coil is adapted to couple to a source of energy that is external to the patient's body, to provide electrical power for energizing electrical components of the band. In one embodiment, the coil is disposed within the wall of the cuff and comprises an insulated wire formed in a plurality of loops. In another embodiment, the coil is adapted to be implanted under a dermal layer in the patient's body and to be electrical connected to the flow transducer. In either case, the coil is adapted to electromagnetically couple to an external coil that is connected to the source of energy.

The receiver preferably comprises the first flow transducer. The radio frequency signal is then applied to the plurality of element as a pulse, causing the plurality of ultrasonic waves to be emitted as a pulse. In this case, the plurality of elements comprising the first transducer receive an echo of the pulse of the ultrasonic waves that is reflected from the blood to determine the parameter based on a Doppler effect.

Another aspect of the present invention is directed to an artificial cardiac valve that monitors blood flow therethrough to determine a condition of the cardiac valve after it is mounted in a patient's heart. The artificial cardiac valve includes a movable valve element, which in a first position, enables blood to flow in a desired direction through the artificial cardiac valve, but in a second position, blocks blood flow therethrough in an opposite direction. A generally annular support is provided for the valve element. A flow transducer is disposed within the support and is oriented to monitor flow through the artificial cardiac valve within a portion of a chamber in a patient's heart. The flow transducer produces a signal indicative of blood flow through the artificial cardiac valve during a cardiac cycle. The blood flow can be evaluated to determine a condition of the artificial cardiac valve. The signal is adapted to couple through a radio link to an external monitoring site that is outside the patient's body to enable the condition of the artificial cardiac valve to be monitored by medical personnel at least from time to time.

An additional transducer is preferably disposed with the support and is oriented to monitor flow through the artificial cardiac valve in a different portion of the chamber, producing an additional signal that is adapted to couple with the external monitoring device through the radio link. The additional signal is further indicative of blood flow through the artificial cardiac valve and is employed to better determine the blood flow through the valve. By using both flow transducers, the condition of the artificial cardiac valve can be more completely evaluated.

An antenna coil is disposed within the support in one embodiment. The antenna coil is used to couple energy from an external source into the flow transducer to energize it and to transmit the signal produced by the flow transducer to the external monitoring device.

In another embodiment, an implanted antenna coil is adapted to be disposed within the patient's body, outside the patient's heart and apart from the flow transducer, but connected thereto. The implanted antenna coil is also used to couple energy from an external source into the flow transducer to energize it and to transmit the signal produced by the flow transducer to the external monitoring device.

If multiple flow transducers are used, a multiplexer is coupled to the flow transducers and is adapted to successively couple the signals produced by the flow transducers to the radio link and the energy received from the external coil to the flow transducers to energize them.

In one preferred form of the invention, each flow transducer produces range-gated pulsed Doppler ultrasonic pulses that are usable to determine blood flow velocity through the cardiac valve. When the artificial cardiac valve is mounted in a patient's heart, the ultrasound beams produced by the one or more flow transducers are directed into a cardiac chamber disposed upstream from the artificial cardiac valve.

Other aspects of the present invention are directed to methods that include steps generally consistent with the functions implemented by components of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

The present invention is employed for monitoring the status of fluid flow through a vessel or cardiac valve and is disclosed in connection with a preferred application in which the flow through a cardiac vessel to determine the condition of a cardiac valve and to monitoring the flow through an artificial cardiac valve to determine its condition. However, it is not intended that the invention be limited to that application. Although much of the following disclosure relates to that medically related application of the invention, it is also contemplated that various aspects of the present invention are also applicable to monitoring the status of fluid flow through any type of vessel, including without limitation, fluid flow through a vessel employed in an industrial process.

Employment of the present invention in the above-noted medical application addresses the problems noted above in the Background of the Invention. Specifically, if the status of fluid flow through a cardiac valve using a transducer is to be monitored for an extended period of time, the system used for this purpose will very likely need to receive energy from an external source and must convey data indicating the status of fluid flow through the vessel and or cardiac valve to an external monitoring device that is disposed outside the patient's body. In many cases, it may be desirable to monitor the status of flow through multiple transducers on different cardiac vessels or in different cardiac valves or at multiple locations on a single cardiac valve. Thus, the data signal indicating the status of fluid flow sensed by each separate transducer must be selected to monitor the condition of fluid flow at each location of a transducer. However, in some cases, only a single transducer may be required to monitor a parameter such as flow or velocity, which is indicative of the internal condition of the cardiac valve.

Figure 1:
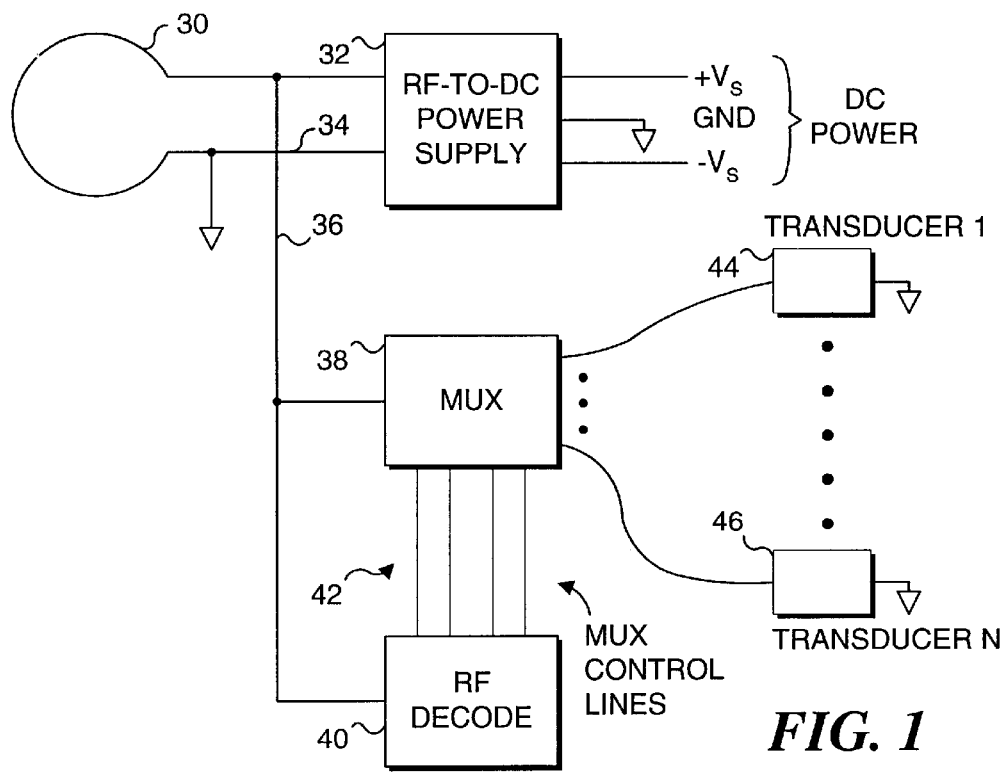
FIG. 1 is a block diagram showing a first embodiment of an implanted electronic circuit for monitoring the status of a cardiac valve with a selected transducer from among a plurality of transducers.

FIG. 1 illustrates a first embodiment of an implanted electronics system for monitoring flow, applicable to the situation in which n transducers are included on one or more bands around cardiac vessel and/or one or more artificial cardiac valves implanted in the patient's body. Variations of the electronic circuit shown in FIG. 1 are discussed below to accommodate specific conditions. In addition, other embodiments of electronic circuits are illustrated in FIGS. 2–6. These embodiments, like that of FIG. 1, are useful for providing power to transducers that monitor fluid flow or velocity through a valve or through a cardiac vessel, and for transmitting data signals from the transducers outside a patient's body to an external remote monitoring console. Some of these circuits are better suited for certain types of measurements than others, and again, variations in the implanted electronic circuits are discussed below, as appropriate.

Each of the circuits shown in FIGS. 1–6 are intended to be implanted within the patient's body and left in place at least during the period in which the flow conditions through one or more cardiac valves or vessels are monitored to determine the status or condition of the cardiac valve(s). Although separate functional blocks are illustrated for different components of the implanted electronic circuits in these Figures, any of the implanted electronic circuits can be implemented in one or more application specific integrated circuits (ASICs) to minimize size and cost, which is particularly important when the electronic circuits are integral with a cuff or band that is coupled around a cardiac blood vessel. The implantable electronic circuits can be either included within the wall of an artificial cardiac valve, or may be simply affixed to or implanted adjacent to a cardiac vessel.

Each of the circuits shown in FIGS. 1–6 includes an RF coupling coil 30, which is connected through lines 34 and 36 to an RF-to-DC power supply 32. This power supply recti- fies and filters an RF excitation signal supplied from an external source to RF coupling coil 30, providing an appropriate voltage DC power signal for the other components of the circuits illustrated in these Figures. In the simplest case, the RF-to-DC power supply would only require rectifiers and filters as appropriate to provide any needed positive and negative supply voltages, +Vs and −Vs. However, it is also contemplated that the power supply may provide for a DC-to-DC conversion capability in the event that the electromagnetic signal coupled into RF coupling coil 30 is too weak to provide the required level of DC voltage for any component. This conversion capability would increase the lower voltage produced by the direct coupling of the external RF excitation signal received by the RF coupling coil, to a higher DC voltage. Details of the RF-to-DC power supply are not shown, since such devices are well known to those of ordinary skill in constructing power supplies. It is also contemplated that it may be necessary to limit the maximum amplitude of the RF input signal to the RF-to-DC power supply to protect it or so that excessive DC supply voltages are not provided to the other components. Alternatively, each component that must be provided with a limited DC voltage supply may include a voltage limiting component, such as a zener diode or voltage regulator (neither shown).

The RF-to-DC power supply may include a battery or a capacitor for storing energy so that it need not be energized when monitoring the flow status, or at least, should include sufficient storage capability for at least one cycle of receiving energy and transmitting data outside the patient's body. Although a storage battery can be included, size limitations may prohibit any significant storage capacity. Instead, a relatively small capacitor could provide the required storage capability. Neither a battery or power storage capacitor are illustrated in the Figures, since they are well known to those of ordinary skill and are only optional.

An additional element that is common to each of the circuits shown in FIGS. 1–6 is an RF decode section 40, which is used for generating control signals that are responsive to information encoded in the external RF excitation signal received by RF coupling coil 30. This information can be superimposed on the RF excitation signal, e.g., by amplitude or frequency modulating the signal received.

Figure 2:
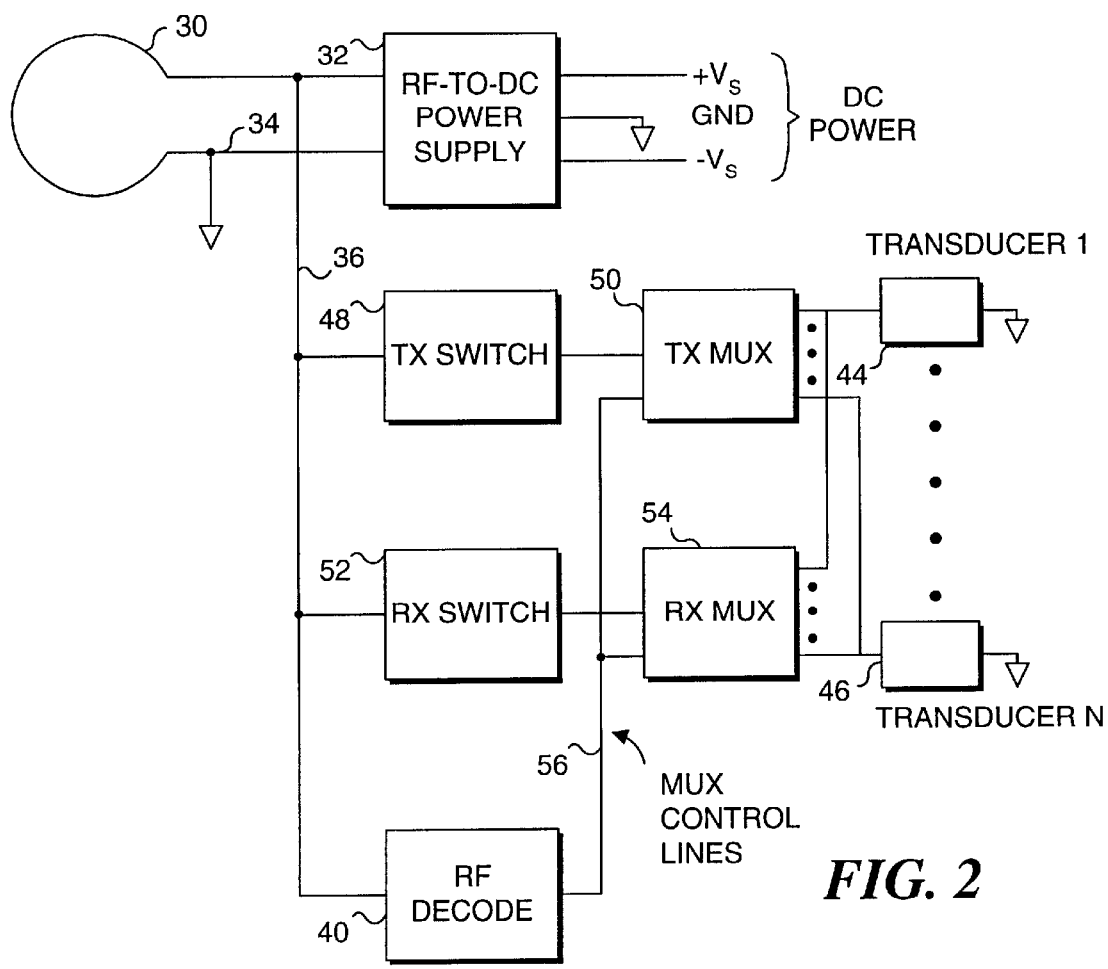
FIG. 2 is a block diagram of a second embodiment of an implanted electronic circuit for monitoring the status of a cardiac valve using separate multiplexers for transmit and receive functions.
Figure 3:
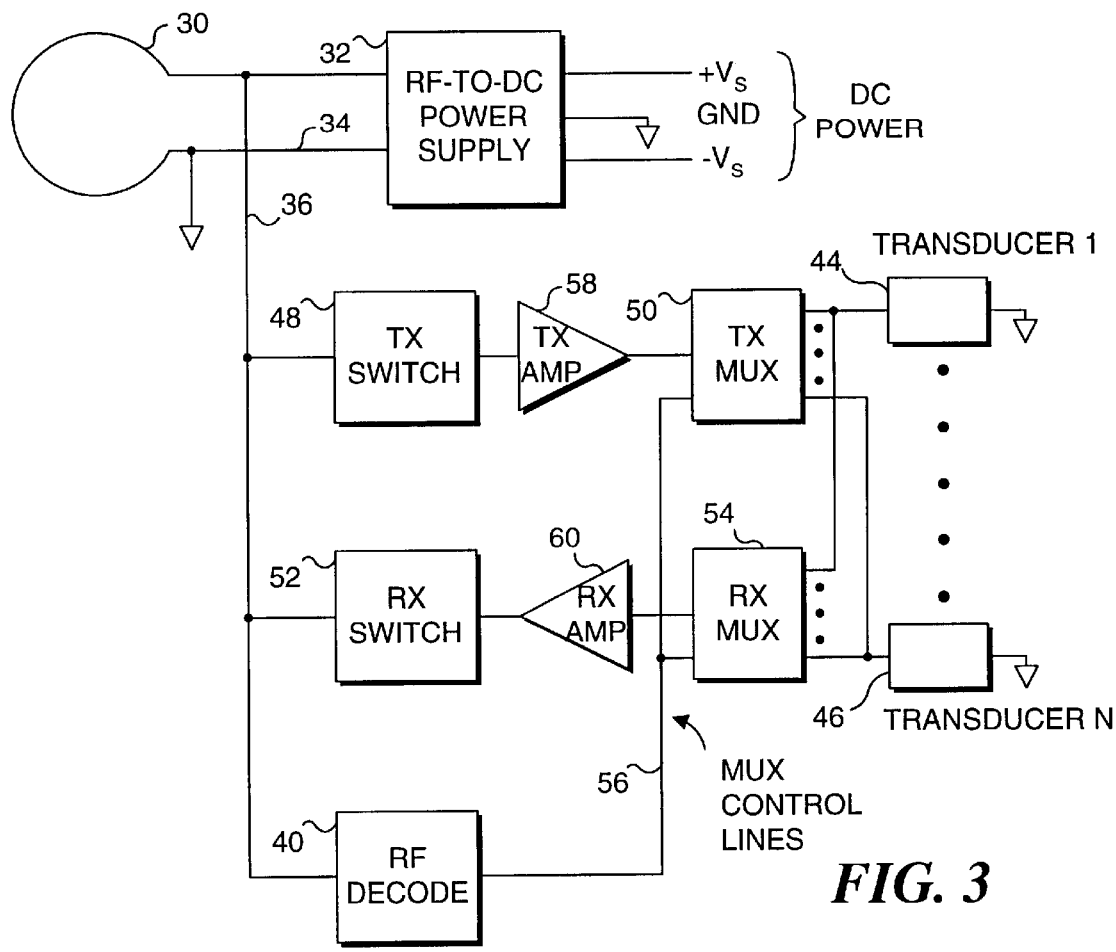
FIG. 3 is a block diagram of a third embodiment of an implanted electronic circuit for monitoring the status of a cardiac valve using separate multiplexers and amplifiers for transmit and receive functions.

In regard to the circuits shown in FIGS. 1–3, the RF excitation frequency is the same as the frequency used to excite a selected ultrasonic transducer to produce an ultrasonic wave that propagates through a vessel or in a chamber of the heart, stream of an artificial cardiac valve being monitored, and for conveying data from a transducer that receives the ultrasonic waves. This approach generally simplifies the implantable electronic circuitry but may not provide optimal performance. Therefore, FIGS. 4 and 5 disclose implantable electronic circuitry in which the RF excitation frequency used to provide power to the RF-to-DC power supply and to provide control signals to RF decode section 40 is decoupled from the frequency that is used for exciting the transducers and modulating the data that they provide for transmission to a point outside the patient's body.

Details of the Implantable Electronic Circuits

Referring now to FIG. 1, line 36 from RF coupling coil 30 is connected to a multiplexer (MUX) 38 to convey signals from a selected one of a plurality of n transducers 44–46 that are coupled to the MUX. To select the transducer that will provide the data signal related to the status of flow through the cardiac valve or cardiac vessel being monitored, RF decode section 40 provides a control signal to MUX 38 through MUX control lines 42. The control signal causes the MUX to select a specific transducer that is to be excited by the RF signal received by RF coupling coil 30 and further, causes the MUX to select the transducer that will provide the data signal for transmission outside the patient's body via RF coupling coil 30.

The implantable electronic circuit shown in FIG. 1 is perhaps more applicable to the Doppler type of ultrasonic transducer for use in monitoring fluid velocity through a cardiac vessel or inside a chamber of the heart, adjacent to an artificial cardiac valve that includes the present invention. If a single-vessel pulse Doppler transducer is used, the same transducer can be used for both transmission and reception of the ultrasonic wave, thereby eliminating the need for MUX 38. In the event that the transducers shown in FIG. 1 are used for transit time flow measurements, it will normally be necessary to use MUX 38 to switch between the transducer used for transmitting the ultrasonic wave and that used to receive the ultrasonic wave, which may present some problems in connection with switching speed, power consumption, and switching transient recovery.

For a single-vessel transit time measurement, a pair of opposed transducers that are disposed on opposite sides of the vessel or opposite side of the artificial cardiac valve are typically used. In order to acquire bidirectional fluid flow data, the direction of the ultrasound wave propagation must be known, i.e., the direction in which the ultrasound wave propagates relative to the direction of fluid flow through the vessel. In this case, MUX 38 is required. However, for single-vessel applications in which the fluid flow is in a single known direction, such as through a cardiac vessel, the transducers that are disposed on opposite sides of the vessel can be electrically connected in parallel or in series, eliminating any requirement for MUX 38. The RF-to-DC power supply and RF decode sections could also then be eliminated, since the retarded and advanced transit time signals would be superimposed on the same RF waveform transmitted by RF coupling coil 30 outside the patient's body. Although this modification to the implantable electronic circuit shown in FIG. 1 would not permit the direction of fluid flow through a cardiac vessel to be determined, the retarded and advanced transit time signals would interfere as they propagate in time, and their interference can be used to estimate the magnitude of fluid flow through the cardiac vessel.

In FIG. 2, an implantable electronic circuit is shown that uses a transmit multiplexer (TX MUX) 50 and a receive multiplexer (RX MUX) 54. In addition, a transmit (TX) switch 48 and a receive (RX) switch 52 couple line 36 to TX MUX 50 and RX MUX 54, respectively. RF decode section 40 responds to instructions on the signal received from outside the patient's body by producing a corresponding MUX control signal that is conveyed to TX MUX 50 and RX MUX 54 over MUX control lines 56 to select the desired transducers.

When ultrasonic signals are being transmitted by one of the selected transducers 1 through n, TX switch 48 couples the RF excitation signal received by RF coupling coil 30 to the transducer that is transmitting the ultrasonic signal, which is selected by TX MUX 50. The TX switch is set up to pass excitation signals to the selected transducer only if the signals are above a predetermined voltage level, for example, 0.7 volts. Signals below that predetermined voltage level are blocked by the TX switch. Similarly, RX switch 52 connects the transducer selected by RX MUX 54 to RF coil 30 and passes only signals that are below the predetermined voltage level, blocking signals above that level. Accordingly, the RF signal used to excite a first transducer selected by TX MUX 50 passes through TX switch 48 and the lower amplitude signal produced by a second transducer selected by RX MUX 54 in response to the ultrasonic signal transmitted through the cardiac vessel, or from an artificial cardiac valve through a heart chamber is conveyed through RX MUX 54 and RX switch 52 and transmitted outside the patient's body through RF coil 30.

The implantable electronic circuit shown in FIG. 3 is similar to that of FIG. 2, but it includes a transmit amplifier (TX AMP) 58 interposed between TX switch 48 and TX MUX 50, and a receive amplifier (RX AMP) 60 interposed between RX MUX 54 and RX switch 52. TX AMP 58 amplifies the excitation signal applied to the transducer selected by TX MUX 50 for producing the ultrasonic wave that is propagated through a cardiac vessel wall. Similarly, RX AMP 60 amplifies the signal produced by the transducer selected by RX MUX 54 before providing the signal to the RX switch for transmission outside the patient's body. Again, the circuit shown in FIG. 3 is most applicable to transit time flow measurements and employs the same frequency for both the RF excitation signal that supplies power to RF-to-DC power supply 32 and the signal applied to a selected one of transducers 44–46 to generate the ultrasonic wave propagating through the cardiac vessel wall, or from the artificial cardiac valve within a heart chamber.

Figure 4:
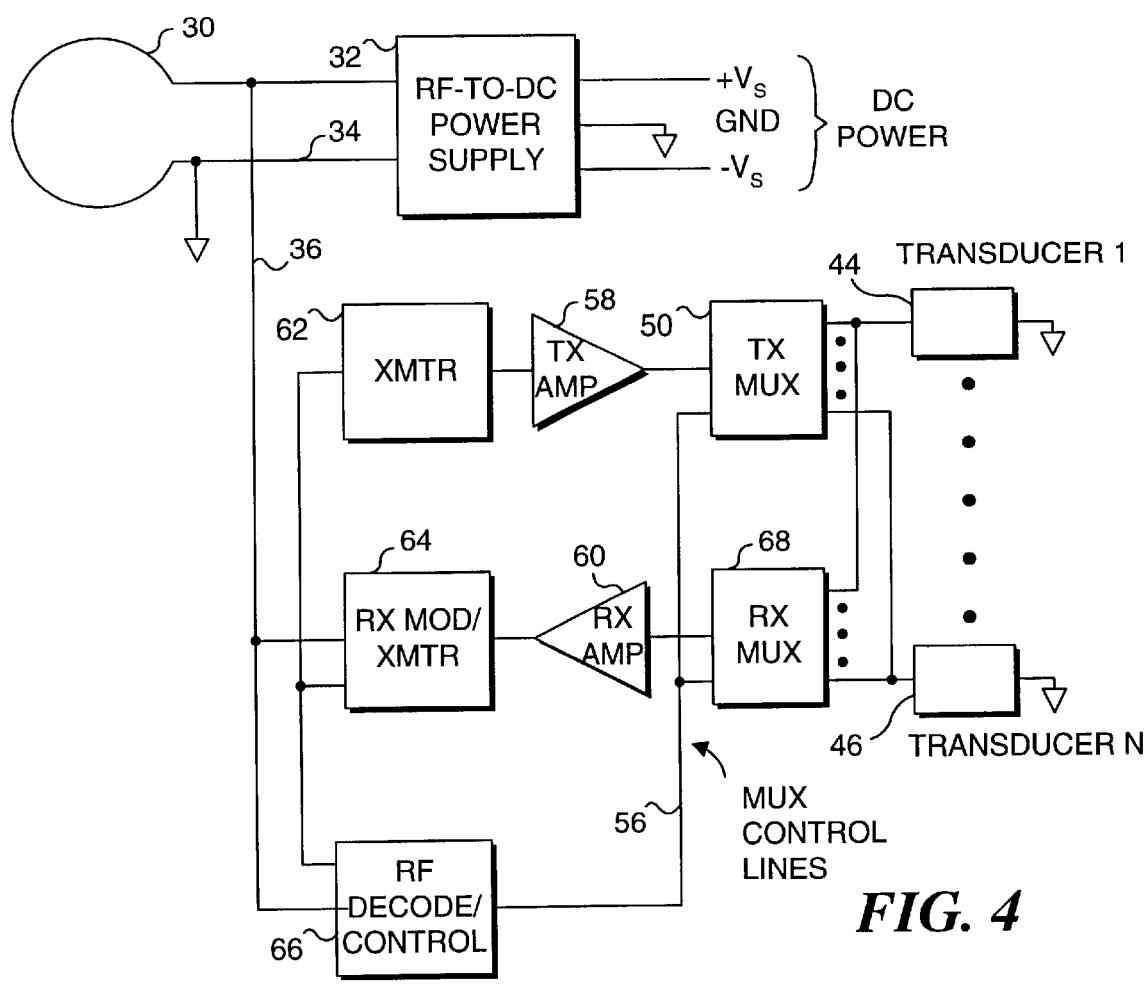
FIG. 4 is a block diagram of a fourth embodiment of an implanted electronic circuit for monitoring the condition of a cardiac valve that employs a local transmitter to excite a selected transducer, and a modulator/transmitter for transmitting signals from the transducers.

In contrast to the implantable electronic circuits shown in FIGS. 1–3, the circuit shown in FIG. 4 enables the RF excitation frequency applied to RF-to-DC power supply 32 to be decoupled from the signal applied to excite any selected one of transducers 44–46. Similarly, the signal produced by the transducer receiving the ultrasonic waves propagating through the heart chamber or cardiac vessel wall is at a different frequency than the RF excitation frequency. In FIG. 4, a transmitter (XMTR) 62 and a receive modulator/transmitter (RX MOD/XMTR) 64 are coupled to and controlled by an RF decode/control section 66. The RF decode/control section determines when the excitation frequency is generated for application to a selected transmit transducer and when the signal produced by the transducer selected to receive the ultrasonic wave is used for modulating the RF signal applied to RF coupling coil 30. An advantage of this approach is that the RF power delivered to RF coupling coil 30 is at an optimal frequency for penetration through the patient's body, thereby improving the efficacy with which the RF energy couples to a specific depth and location within the body. Another reason is for satisfying any requirements for selecting a particular frequency to comply with RF allocation bands for medical equipment. Similarly, the frequency applied to any selected transducers 44 and 46 to stimulate their production of ultrasonic waves can be optimal for that purpose. Assuming that the two frequency bands, i.e., the RF excitation frequency band for the signal applied to the power supply and the frequency band applied to excite the transducers, are sufficiently separated, the RF power delivery can occur simultaneously with the excitation of a selected transducer and the reception of the ultrasonic waves by another selected transducer. Accordingly, more RF power can be coupled into the system from the external source than in the implantable electronic circuits shown in FIGS. 1–3.

The control signals that are supplied to RF decode/control section 66 via RF coupling coil 30 can be conveyed using nearly any kind of modulation scheme, e.g., by modulating the RF excitation that powers the device, or by sending a control signal on a separate and distinct RF frequency. Also, the signals that are received from the transducer in response to the ultrasonic wave that is propagated through the heart chamber or cardiac vessel wall can be transmitted through the RF coupling coil at a different frequency than the incoming excitation frequency, thereby eliminating interference between the power supply and data signal transmission functions.

The implantable electronic circuit shown in FIG. 4 is most applicable to transit time flow measurements in which pairs of transducers are selected for transmitting and receiving the ultrasonic wave that propagates along one or more directions within a cardiac chamber or through one or more cardiac vessel walls on which the transducers are installed. RF decode/control section 66 can be employed to control TX MUX 50 and an RX MUX 68 to interchange the transducers used for transmission and reception of the ultrasonic wave on successive pulses. Using this technique, the direction of the ultrasonic wave propagation through the cardiac chamber or cardiac vessel is changed on alternating pulses of ultrasonic waves, enabling transit time difference information to be gathered without requiring further multiplexer programming information to be transmitted between successive ultrasonic wave pulses. This approach greatly improves the data gathering efficiency of the implantable electronic circuit shown in FIG. 4 compared to the previously described implantable electronic circuits of FIGS. 1–3.

Figure 5:
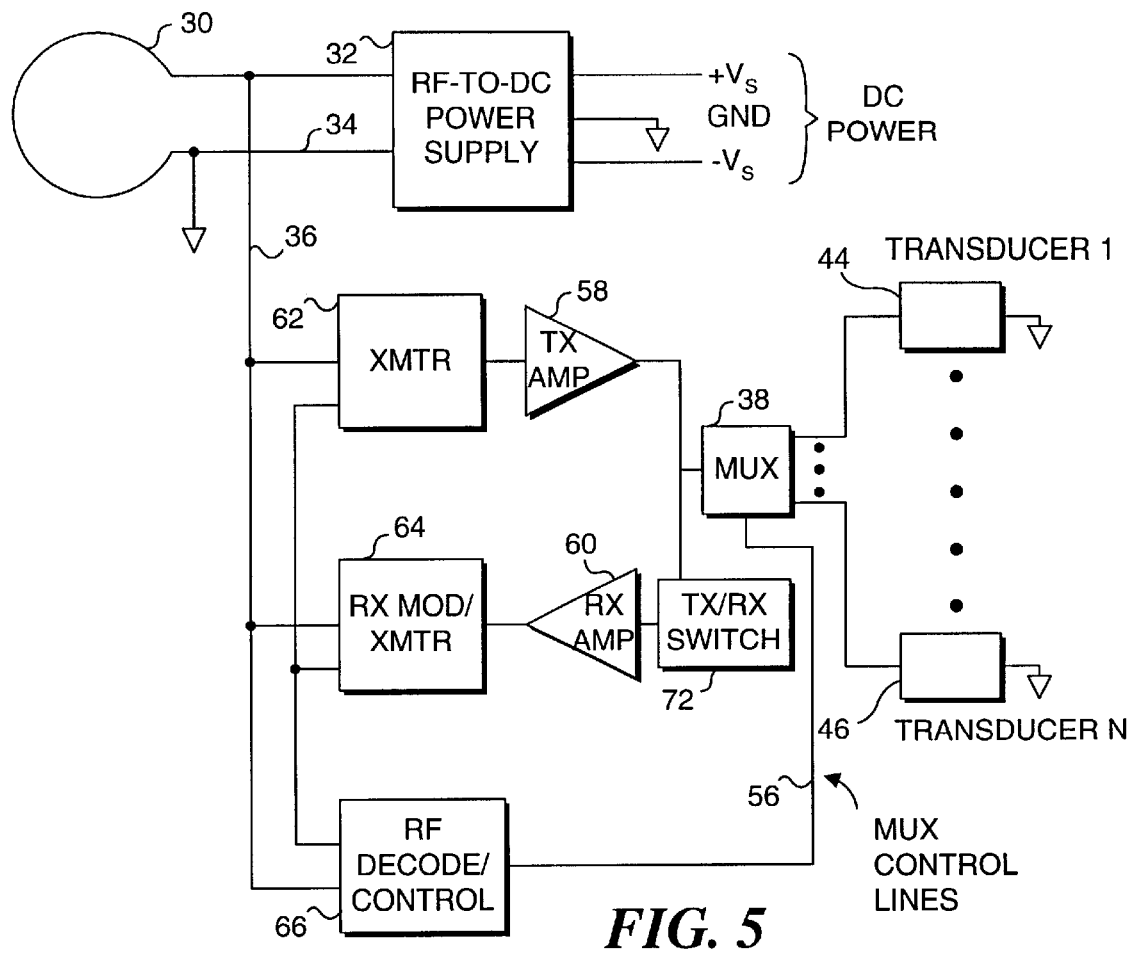
FIG. 5 is a block diagram of a fifth embodiment of an implanted electronic circuit for monitoring the status of a cardiac valve, where one transducer is selected for transmitting and receiving, and a modulator/transmitter is used for transmitting the signal produced by the receiving transducer.

To further improve the implantable electronic circuit shown in FIG. 4 for use in sensing fluid velocity through a heart chamber or cardiac vessel using a Doppler technique, the modification shown in FIG. 5 is made. In the latter implantable electronic circuit, a TX/RX switch 72 is added so that the circuit transmits and receives through the same transducer. As a result, separate transmit and receive multiplexers are not required. Instead, MUX 38 is used to select the specific transducer for receiving the RF excitation signal produced by XMTR 62 so that the transducer produces an ultrasonic wave and then receives the echo from fluid flowing through the artificial cardiac valve or cardiac vessel to produce a receive data signal that is output through RX MOD/XMTR 64. TX/RX switch 72 prevents the signal applied by TX AMP 58 from overdriving the input to RX AMP 60, effectively isolating the RX AMP during the time that the RF signal is applied to the transducer to excite it so that it produces the ultrasonic wave. However, the echo signal received by the transducer is allowed to reach RX AMP 60 when TX/RX switch 72 changes state (from transmit to receive). Generally, the implantable electronic circuit shown in FIG. 5 has the same benefits as described above in connection with the circuit. shown in FIG. 4. RF decode/control section 66 responds to the information received from outside the patient's body that determines which one of transducers 44–46 is selected at any given time by producing an appropriate MUX control signal that is supplied to MUX 38 over MUX control lines 56.

It is also contemplated that RF decode/control section 66 may cause MUX 38 to select a different transducer for producing/receiving the ultrasonic waves after a predefined number of transmit/receive cycles have elapsed. For example, a different transducer may be selected after eight cycles have been implemented to transmit an ultrasonic wave into the heart chamber or cardiac vessel and to receive back the echoes from the fluid flowing through the heart chamber or cardiac vessel. By collecting data related to the status of flow through one or more cardiac valves or cardiac vessels in this manner, it becomes unnecessary to send programming information to RF decode/control section 66 after each cycle of a transmission of the ultrasonic wave into the fluid in the heart chamber or cardiac vessel and reception of the echo. By carrying out a predefined number of transmit/receive cycles for a given transducer that has been selected by MUX 38 and averaging the results, a more accurate estimate of fluid velocity through the cardiac vessel can be obtained than by using only a single transmission and reception of an ultrasonic wave. Since the signal required to instruct RF decode/control section 66 to change to the next transducer is only required after the predefined number of cycles has been completed, the data gathering efficiency of the implanted electronic circuit is improved.

Figure 6:
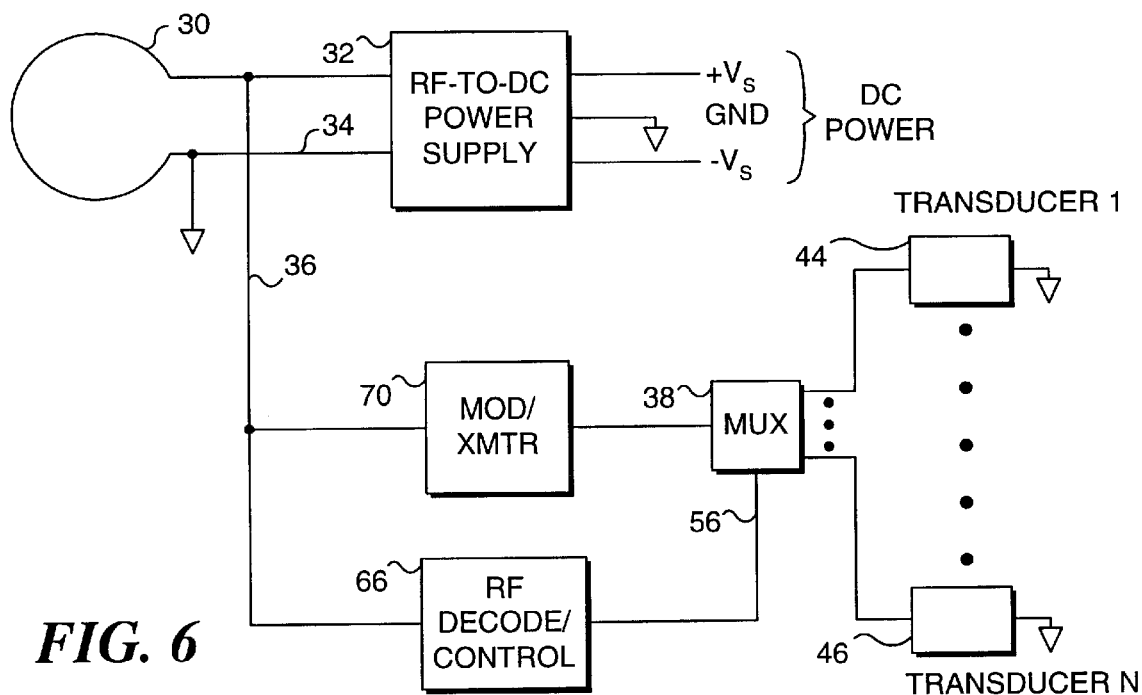
FIG. 6 is a block diagram of a sixth embodiment of an implanted electronic circuit for monitoring the status of a cardiac valve, wherein one of a plurality of transducers is selectively coupled to a modulator/transmitter for transmitting a signal indicative of fluid pressure or other parameters.

Although transducers 44–46 that are shown in FIGS. 1–5 need not be ultrasonic transducers, FIG. 6 illustrates an implantable electronic circuit that is particularly applicable for use with transducers 44–46 comprising pressure sensors. For example, such pressure sensors could be disposed within the wall of an artificial cardiac valve to sense the pressure of fluid flowing through the valve at one or more points. MUX 38 is used for selecting a specific pressure transducer to provide a data signal that is transmitted to the outside environment via RF coupling coil 30. In this circuit shown in FIG. 6, a modulator/transmitter (MOD/XMTR) 70 receives the signal from the transducer selected by MUX 38 in response to the MUX selection signal provided over MUX control lines 56 from RF decode/control section 66 and using the signal, modulates an RF signal that is supplied to RF coupling coil 30. The RF signal transmitted by coupling coil 30 thus conveys the data signal indicating pressure sensed by the selected transducer. In most cases, parameters such as fluid flow or velocity are better indicators of the condition of a cardiac valve.

RF Coupling Coil and External Coil Embodiments

FIGS. 7–10 illustrate details of several different embodiments for the RF coupling coil that is implanted within a patient's body for receiving RF energy to provide power for the implanted electronic circuits discussed above and for transmitting data relating to the condition of flow through one or more artificial cardiac valves or cardiac vessel monitoring cuffs that have been installed within the patient's body. Optimization of RF coupling between the RF coupling coil that is implanted and the external coil is partially dependent upon the propagation characteristics of the human body. Since body tissue is largely comprised of water, the relative dielectric constant of flesh is approximately equal to that of water, i.e., about 80. Also, the permeability of tissue comprising a body is approximately equal to one, i.e., about that of free space. The velocity of propagation of an RF signal through the body is proportional to the inverse square root of the dielectric constant and is therefore about 11% of the velocity of the signal in free space. This lower velocity reduces the wavelength of the RF signal by an equivalent factor. Accordingly, the wavelength of the RF signal transferred between the implanted RF coupling coil and the external coil would be a design consideration if the separation distance between the two is approximately equal to or greater than one-quarter wavelength. However, at the frequencies that are of greatest interest in the present invention, one-quarter wavelength of the RF coupling signal should be substantially greater than the separation distance between the two coils.

The penetration of RF fields in the human body has been studied extensively in conjunction with magnetic resonance imaging (MRI) systems. RF attenuation increases with frequency, but frequencies as high as 63 MHz are routinely used for whole body imaging, although some attenuation is observed at the center of the torso at the upper end of the frequency range. In addition, MRI safety studies have also provided a basis for determining safe operating limits for the RF excitation that define the amplitude, which can be safely applied without harm to the patient.

It is contemplated that for cardiac vessel flow monitoring cuff implants placed deep within the body of a patient, and for artificial cardiac valves that include ultrasonic transducers, RF excitation and frequencies used for communicating data related to the fluid flow cardiac valve or cardiac vessel can be up to about 40 MHz, although higher frequencies up to as much as 100 MHz may be feasible. At 40 MHz, the wavelength of the RF excitation signal in tissue is about 82 cm, which is just that point where wavelength considerations become an important consideration. For shallow RF antenna implants, RF excitation at a much higher frequency may be feasible. To provide energy to the implanted electronic circuit and to receive data from transducers associated with such antennas, frequencies in the range of a few hundred MHz may be useful. The dielectric properties of tissue have been studied to at least 10 GHz by R. Pethig, *Dielectric and Electronic Properties of Biological Materials*, Wiley Press, Chichester, 1979 (Chapter 7). Based on this study, no penetration problems are anticipated in the frequency range of interest. The dielectric constant of tissue decreases to about 60 at a frequency of 100 MHz and is about 50 at 1 GHz, but this parameter has little effect on power/data signal coupling.

Figure 7:
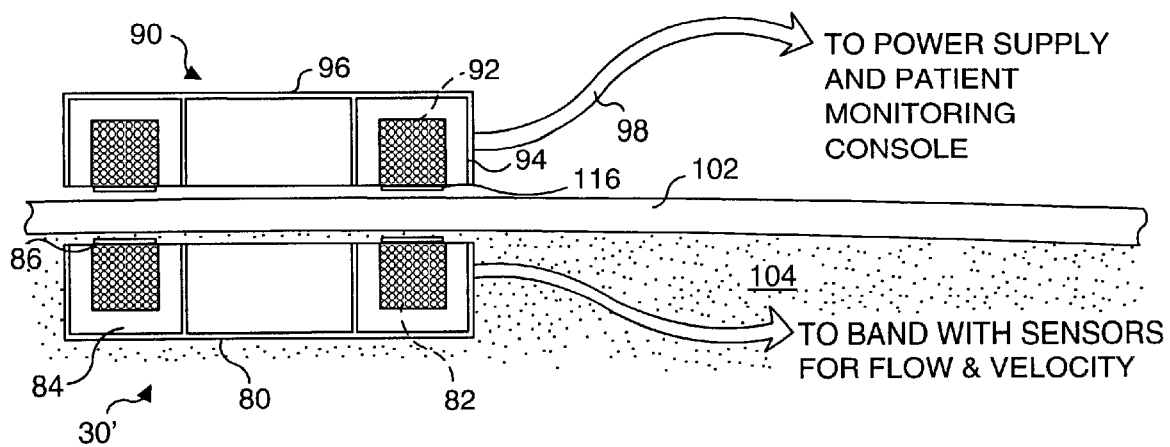
FIG. 7 is a cross-sectional view of an implanted radio frequency (RF) coupling coil and an external coil.

In FIG. 7, an RF coupling coil 30' is disposed opposite a corresponding external coil 90. RF coupling coil 30' includes a toroidal coil 82 that is wound in the hollow center channel of a toroidal-shaped core 84. Core 84 and toroidal coil 82 are contained within a biocompatible housing 80 that also provides RF shielding around the coil except where it lies opposite to external coil 90. External coil 90 is of similar design, including a toroidal coil 92 disposed within the hollow center portion of a toroidal-shaped core 94. A housing 96 comprising an RF shield encloses much of the toroidal coil and core. A cable 98 conveys signals to and from an external power supply and patient monitoring console 100, which is shown in FIG. 8.

Figure 8:
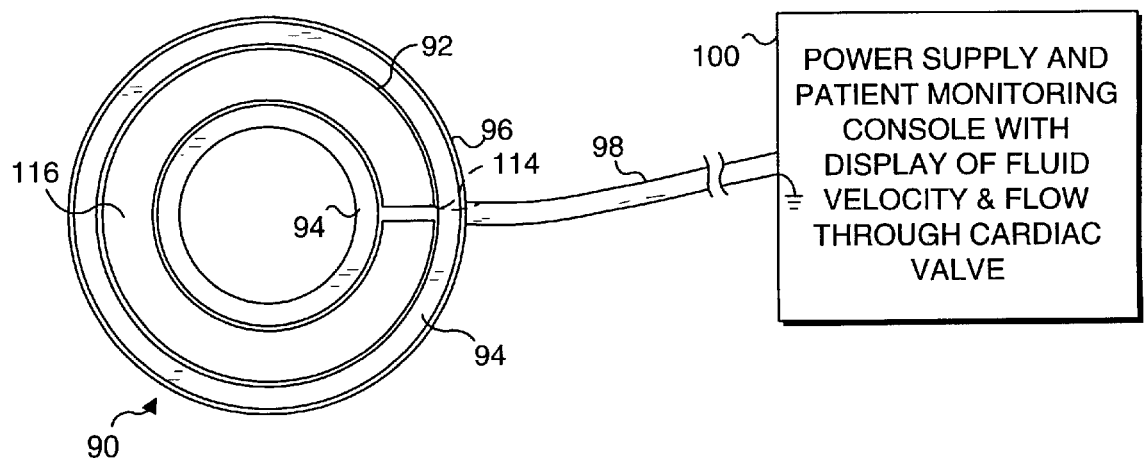
FIG. 8 is a bottom view of the external coil shown in FIG. 7.

The external coil and RF coupling coil shown in FIGS. 7 and 8 represent one embodiment used for coupling electrical energy and conveying data signals across a skin interface 102 for applications in which the RF coupling coil is implanted relatively close to the surface of the skin. For example, RF coupling coil 30' and external coil 90 would provide the coupling required for a system used to monitor the condition of an artificial cardiac valve that does not include an internal RF antenna coil. During surgery to implant an artificial cardiac valve, a patient's chest is opened, making it relatively straightforward to implant RF coupling coil 30' beneath the skin as the chest is being closed.

Although the external core and internal core need not be identical in size and shape, it is generally true that coupling will be optimal if the annular surfaces of the two cores are of approximately the same dimensions and if the core halves are aligned. By observing the strength of the signal transmitted from RF coupling coil 30', it should be possible to position external coil 90 in proper alignment with the implanted coil so that the amplitude of the signal is maximized.

To function as a transformer core, the material used must have a relatively high magnetic permeability, at least greater than one. Although ferrite is commonly used for core materials, sintered powdered iron and other alloys can also be used. Since the choice of materials for the cores of the. RF coupling coil and the external coil based on the magnetic characteristics of such materials are generally well understood by those of ordinary skill in the art, further details need not be provided herein to provide an enabling disclosure of the present invention.

Housing 96 on external coil 90 provides RF shielding against electromagnetic interference (EMI). Housing 96 is preferably conductive, grounded, and surrounds the external coil except where the face of core 84 is opposite core 94 of the implanted coupling coil. The RF shield comprising housing 96 also includes a split annular ring 116, which is attached to the internal shield (not separately shown) at cable 98. A similar split annular ring 86 is provided on RF coupling coil 30' covering toroidal core 82. Split annular rings 86 and 116 are used so that a shorted turn is avoided that would otherwise tend to attenuate a coupling between the external coil and RF coupling coil. The housing of the implanted coupling coil is connected to the shield on the cable, and the shield is connected to a shield on the cuff that includes the ultrasonic flow sensors to monitor flow through a cardiac vessel. Inside power supply and patient monitoring console 100, the shield on cable 98 is connected to ground. The RF shields on both the external coil and the RF coupling coil that is implanted within the patient, along with the shields provided around the transducers (described below) minimize external EMI radiation due to the use of the present invention within a patient's body.

Figure 9:
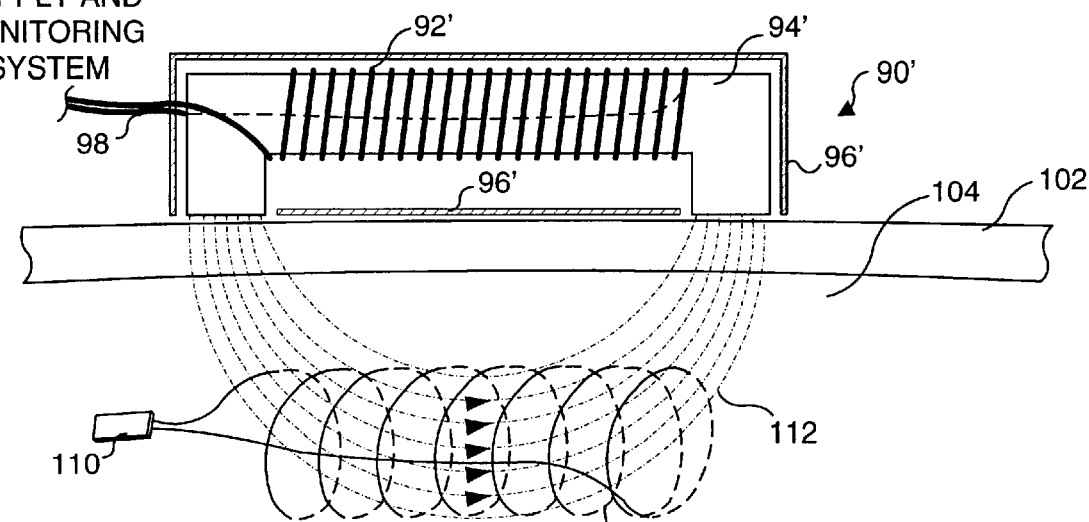
FIG. 9 is a cut-away, side elevational view of an alternative external coil and a side elevational view a spiral RF coupling coil implanted within a patient's body.

Referring now to FIG. 9, a plurality of spiral conductor coils 108 are shown for coupling RF energy and data to an electronics assembly 110 used by an implanted cuff disposed around a cardiac vessel or by an artificial cardiac valve that is implanted within a patient's heart. Although the drawing shows only a single layer of spiral coils 108, it is contemplated that a plurality of layers of such coils may be used and that the spacing between the spiral coils may be substantially closer than illustrated in the Figure. Electronics assembly 110 may include any of the implantable electronic circuits shown in FIGS. 1–6. Not shown in FIG. 9 are the transducers that are provided within the wall of the artificial cardiac valve or within the band that is wrapped around a cardiac vessel.

An external coil 90' shown in FIG. 9 has a generally C-shaped core 94' about which is coiled a plurality of turns 92'. Leads 98 pass through a housing 96' that comprises an RF shield and connect the external coil to a power supply and monitoring system (not shown). Lines of magnetic flux 112 intersect spiral coils 108 to provide electrical power for energizing electronics assembly 110. Similarly, spiral coils 108 generate an electromagnetic field that is concentrated along a longitudinal axis of the spiral coils that is,sensed by external coil 90' to convey data indicating the flow status of the fluid through a cardiac valve to the power supply and monitoring system. Alternatively, external coil 90' can be used to couple with an antenna coil included within the wall of an artificial cardiac valve, as will be discussed below.

Core 94' of external coil 90' is preferably fabricated of a ferrite core material, or other suitable alloy. The number of coils 92', the size of the wire, size of the core, and other parameters can be determined for a particular frequency of operation using conventional transformer design criteria, by one of ordinary skill in the art.

Figure 10:
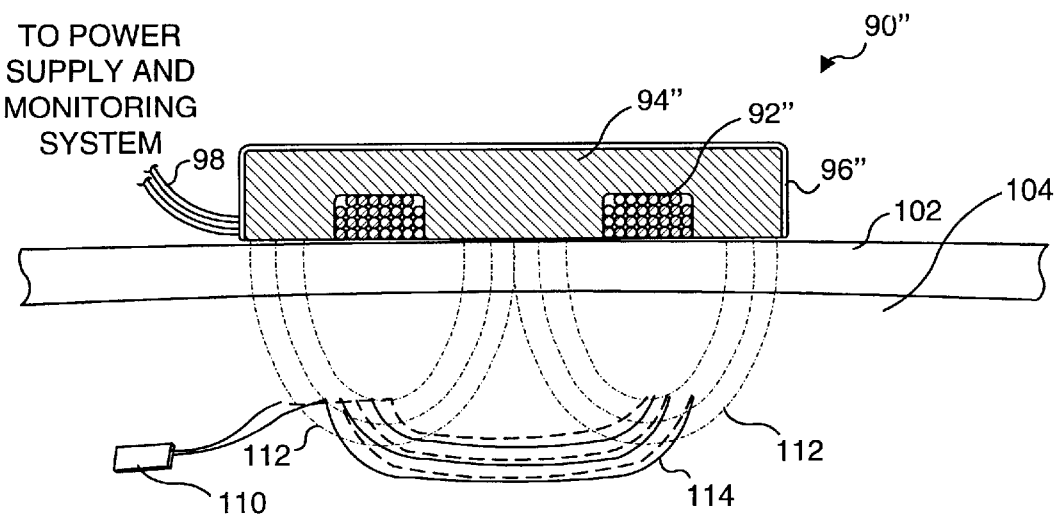
FIG. 10 is a cut-away, side elevational view of a further embodiment of an external coil and a side elevational view of a saddle-shaped RF coupling coil.

In FIG. 10, a plurality of generally saddle-shaped coils 114 are implanted within a patient's body, generally below skin interface/dermal layer 102. Again, the RF coupling coil is coupled to electronics assembly 110. Although only a single layer of saddle-shaped coils 114 is illustrated, it is contemplated that a plurality of such interconnected layers could be provided.

An external coil 90" is provided that includes a plurality of coils 92" wrapped around a central portion of a generally E-shaped core 94". Lines of electromagnetic flux are thus produced between the central leg and each of the end legs of core 94". It will therefore be apparent that in this embodiment, the RF coupling coil and the external coil achieve optimum coupling when the distance separating the two is minimal. Therefore, external coil 90" is best used in applications where the implanted saddle-shaped antenna is disposed relatively close to dermal layer 102 so that tissue 104 separating the implanted antenna from external coil 90" is only a few centimeters thick. Maximal coupling is achieved when the longitudinal axis of external coil 90" is aligned with the longitudinal axis of saddle-shaped antenna coils 114.

Description of the Ultrasonic Transducer Arrays

An ultrasonic transducer for monitoring flow or fluid velocity through a cardiac valve or cardiac vessel should be relatively compact if it is to be mounted within the wall of an artificial cardiac valve, or included in a cuff that wraps around a cardiac vessel. Typically, a prior art ultrasonic transducer includes an element comprising a planar slab of a piezoelectric material having conductive electrodes disposed on opposite sides thereof. Since such elements are relatively planar, they do not conform to the circular cross-sectional shape of an artificial cardiac valve or cardiac vessel cuff and therefore, are not compact or appropriate for use with an artificial cardiac valve or cardiac vessel cuff that is implanted within a patient's body and which is intended to be left in place for an extended period of time.

Figure 11:
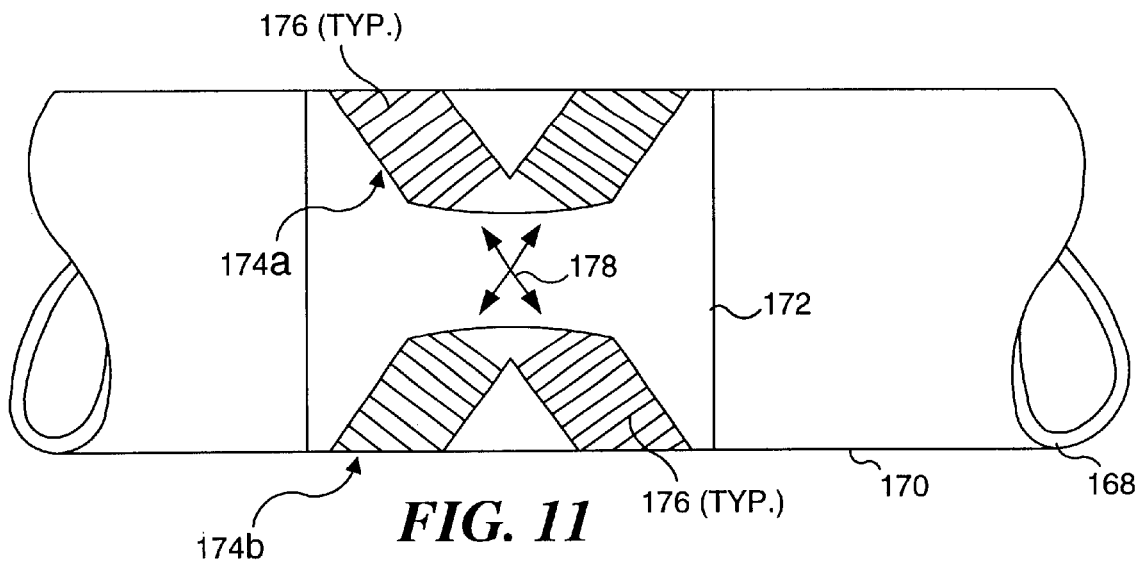
FIG. 11 is a side elevational schematic view of a dual beam conformal transducer array on a carrier band for use around a fluid carrying vessel, in accord with the present invention.

FIG. 11 shows an embodiment of an extremely low profile ultrasonic transducer comprising a conformal array 174*a* disposed on opposite sides of a cardiac vessel 170 from a conformal array 174*b*. Ideally, the conformal array comprises a piezoelectric plastic used as a transduction material and having sufficient flexibility to allow the transducer elements to be wrapped around a wall 168 of vessel 170. Such flexible piezoelectric plastic materials are readily available. It should be noted that vessel 170 is one of the cardiac vessels, and that the transducer is used to monitor the condition of a natural or artificial cardiac valve controlling blood flow through that vessel. However, the compact, low profile aspect of the conformal transducer array makes it ideally suited for other applications outside the medical field. It is therefore contemplated that the conformal array ultrasonic transducer shown in FIGS. 11, 12, and 13 may alternatively be used in other commercial and industrial applications in which space around a vessel wall is at a premium and there is a need to monitor flow and/or velocity of a fluid through the vessel. Thus, the conformal array transducer 10 may be used to monitor fluid flow or velocity through a plastic or metal pipe or tube. Furthermore, it can be used for either transit time or Doppler measurements. When used for transit time measurements, as shown in FIGS. 11 and 12, conformal arrays 174*a* and 174*b* are disposed generally on opposite sides of the vessel and encompass much of the circumference of the vessel.

However, when a pulsed Doppler measurement is made using the conformal array transducer, only a single such transducer is required, since it first produces an ultrasonic wave that is transmitted into the vessel and then receives an echo reflected back from the fluid flowing through the vessel. If used for continuous wave (CW) Doppler measurements, the pair of conformal array transducers disposed on opposite sides of the vessel are again needed, one transducer serving as a transmitter and the other as a receiver. In each case, it is presumed that the fluid has a non-zero velocity component directed along an ultrasonic beam axis of the ultrasonic wave produced by the conformal array transducer serving as a transmitter.

Figure 12:
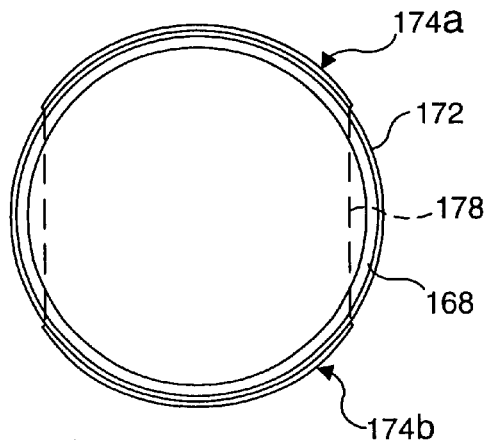
FIG. 12 is an end elevational view of the conformal transducer array of FIG. 11, around a vessel.
Figure 13:
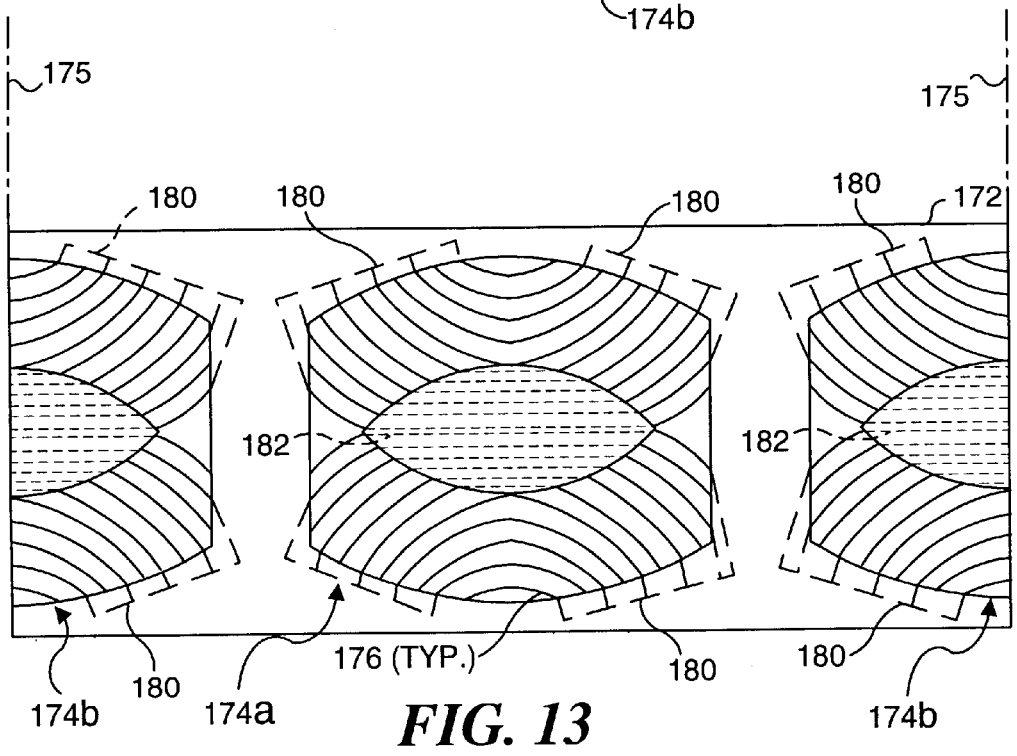
FIG. 13 is a plan view of the conformal transducer array shown in FIGS. 11 and 12, cut along a cut line to display the dual conformal arrays in a flat disposition.

Conformal arrays 174*a* and 174*b* shown in FIGS. 11–13 produce ultrasonic beams 178 that are tilted relative to the transverse direction across vessel 170 in substantially equal but opposite angles with respect to the longitudinal axis of the vessel. Since dual beam transit time measurements are implemented by conformal arrays 174*a* and 174*b*, the results are self-compensating for tilt angle errors. This form of self-compensation is only required where the alignment of the conformal array relative to the longitudinal axis of the vessel may be imperfect. For example, such imperfections are likely to occur when the conformal arrays are used in connection with monitoring the status of fluid flow through cardiac vessels within a patient's body, since the cardiac vessels are not rigid and frequently are not straight—even within the limited length of the conformal array. For transit time measurements made on vessels wherein the alignment of the transducer relative to the longitudinal axis of the vessel is well known, an opposed pair of conformal arrays disposed on opposite sides of the vessel is sufficient so that the added complexity of the dual beam transducer geometry is not required for self compensation.

In the case of pulsed Doppler velocity measurements, a single transducer would again likely be adequate so long as the alignment of the transducer to the vessel is accurately controlled. If the alignment of the conformal array transducer is not controlled or not well known, a second such transducer can be used to gather velocity data along a second beam axis using pulsed Doppler velocity measurements. Assuming that the second axis is tilted in an equal but opposite direction as the first axis, the Doppler measurements made by the two conformal array transducers should be self-compensating for tilt errors. In this case, the second conformal array transducer could be mounted on the same or on an opposite side of the vessel from that where the first conformal array transducer is mounted to implement the Doppler measurements.

For CW or pseudo-CW Doppler velocity measurements (in which a relatively long duration pulse of ultrasonic waves is produced), the transit signal is applied for a sufficiently long period so that a second transducer is needed to receive the echo signals. In this case, a single set of diametrically opposed conformal array transducers can be used.

As perhaps best illustrated in FIG. 12, conformal array transducers 174*a* and 174*b* need not wrap entirely around vessel 170. In the illustrated embodiment, the conformal array transducers each span an arc of approximately 120° around the longitudinal axis of the vessel (i.e., about the center of the circular vessel as shown in FIG. 12). This geometry produces a measurement zone through which ultrasonic beams 178 propagate that is nominally equal to about 87% of the vessel outer diameter. Since vessel wall 168 has a finite thickness, the actual measurement zone (within the lumen of the vessel) exceeds approximately 90% of the vessel internal diameter. If used for Doppler velocity measurements, it is contemplated that the conformal array transducer need cover only a central portion of the vessel. As a result, the span of the conformal array transducer can be reduced from about 120° to something within the range from about 60° to about 90°. This conformal array transducer is particularly useful in determining the condition of a cardiac valve by monitoring flow through a cardiac vessel adjacent to the cardiac valve.

To produce a wide, uniform ultrasound beam such as that needed for transit time measurements of flow, the conformal array transducer must produce ultrasonic waves having a wave front characterized by a substantially uniform amplitude and phase. As shown in FIG. 11, lateral projections through each of a plurality of transducer elements comprising the conformal array transducers are indicated by straight lines 176. These straight lines indicate the centers of the transducer elements and are perpendicular to the axis of propagation of ultrasonic beams 178 (represented by bi-directional arrows directed along the axes of propagation of the ultrasonic waves). In the preferred embodiment, the spacing between the element centers, i.e., between straight lines 176, is approximately equal to a phase angle of 90° at the transducer's excitation frequency. Thus, starting at the top of FIG. 11 and working downwardly, transducer elements disposed along each of the displayed straight lines produce acoustic waves that are successively delayed by 90°, or one-quarter wavelength in the fluid medium through which the ultrasonic waves propagate. For tissue, a sound velocity of 1,540 meters/second is normally assumed, so that the physical spacing of the projected straight lines would typically be defined by the following:

$$\text{Projected Spacing in millimeters} = 1.54/(4F0)$$

where F0 is equal to the center frequency in MHz. If zero degrees is assigned to the top-most element of conformal array 174a, the next element would operate at −90° relative to the top element, followed by an element operating at −180°, and then one operating at −270°, and finally by an element operating at 0° relative to the top electrode. Thus, conformal array 174a produces a succession of ultrasonic waves spaced apart by a 90° space shift, thereby achieving a desired phase uniformity across the transducer.

Amplitude uniformity can be achieved in the ultrasonic wave front by "shaving" the elements of the conformal array. Although shaving could be achieved in a variety of ways, the preferred embodiment controls shaving by varying the area of each element.

Conformal array transducers 174a and 174b are carried on a band 172 preferably made from the piezoelectric plastic material used for the element substrate, which is sized to fit snugly around an outer surface of vessel 170, such as that of a cardiac vessel. Band 172 is intended to position the conformal array transducers in acoustic contact with vessel wall 168. Such contact assures that the ultrasonic waves produced by the element of the conformal array are conveyed through the vessel wall and into the fluid flowing through the interior of the vessel. Preferably, the piezoelectric plastic comprising band 172 is fabricated from a material such as polyvinylidene fluoride (PVDF), poly(vinyl cyanide-vinyl acetate) copolymer (P(VCN/VAc), or poly (vinylidene fluoride-trifluoroethylene) copolymer (P(VDF-TrFE)). Preferably, P(VDF-TrFE) is used because of its superior piezoelectric coupling and relatively lower losses.

Referring now to FIG. 13, further details of the conformal array transducers are illustrated. In this embodiment, alternating elements of the conformal array produce ultrasonic waves differing by 90°. In the view shown in FIG. 13, a cut line 175 intersects the lateral center of conformal array 174b. In practice, any cut would more likely extend through band 172 at a point approximately midway between conformal array 174a and conformal array 174b. If band 172 must be cut in order to wrap the band around vessel 170, i.e., when it is not possible or practical to slip band 172 over the vessel uncut, the elements comprising the conformal array transducers need not be interrupted or damaged. It will be apparent that installation of band 172 around a cardiac vessel is facilitated by cutting the band and then wrapping it around the vessel, unless a surgeon has previously cut through the vessel for some other purpose, such as when installing an artificial cardiac valve. Electrodes comprising each element of the conformal array can be photolithographically generated on the piezoelectric plastic substrate comprising band 172. Alternatively, the elements can be formed on a non-piezoelectric material comprising band 172, and then the material with the elements formed thereon can be bonded to a piezoelectric substrate in each area where a conformal array transducer element is disposed. In this latter embodiment, it is contemplated that a flex circuit material such as a polyimide could be employed for band 172, and that conventional photolithographic processing methods might be used to fabricate the conformal array transducer circuitry on the band. Further, the centers of alternating conformal array elements are coupled together electrically via conductors 180 (shown as dash lines) in FIG. 13. Not shown in FIGS. 11–13 are the leads that extend from an electronics assembly used to drive the conformal array. Any of the implantable electronic circuits shown in FIGS. 1–5 could be used for the electronics assembly.

The pattern of elements comprising each of the conformal array transducers and the boundary of each conformal array (top and bottom as shown in FIG. 13), define sinusoidal segments. The period of the sine wave from which these sinusoidal segments are derived is approximately equal to the circumference of band 172. Further, the amplitude of that sine wave generally depends on the desired beam angle relative to the longitudinal axis of vessel 170. For the sinusoidal segment employed for each electrode, the amplitude is defined by:

$$\text{Amplitude} = D \tan \Theta$$

Similarly, the amplitude of the sinusoidal segment defining the boundary of each conformal array is defined by:

$$\text{Amplitude} = D/(\tan \Theta)$$

where Θ is equal to the angle between the longitudinal axis of the vessel and the ultrasound beam axis and D is equal to the external diameter of the vessel. Accordingly, it should be apparent that one sinusoidal template could be used to draw all of the transducer elements and a second sinusoidal template (differing only in amplitude from the first) could be used to draw the boundary of each conformal array transducer. The transducer elements are displaced or spaced apart from one another as required to achieve the phase relationship described above in connection with FIG. 11. In addition, the actual physical electrode pattern and placement of the elements on band 172 can be determined by finding intersection loci between band 172 as wrapped around vessel 170 and equally-spaced planes. The spacing between these planes is defined by the equation noted above for the projected spacing.

Conductors 180 that connect transducer elements of the same phase differ by 90°. There are two ways to achieve the 90° phase variation between the ultrasonic waves produced by successive electrodes in the conformal array. In the first approach, a uniformly polarized piezoelectric plastic substrate is used and every fourth element is connected together, producing four groups of elements or electrodes that produce ultrasonic waves having phasal relationships of 0°, 90°, 180°, and 270°, respectively. Alternatively, a zone polarized piezoelectric plastic substrate could be used and every other element can be connected together (as shown in FIG. 13). Each of these two groups is then connected to provide an in phase and a quadrature phase transceiving system, so that ultrasonic waves are produced by the elements having a relative phase relationship of 0° and 90°. In the first approach, a multi-layer interconnect pattern is required to connect to all traces for each of the transducer elements in the four groups.

In addition, a more complex four-phase electronic driving system that includes a phase shifter is required. Specifically, the signal applied to each of the four groups must differ by 90° between successive elements to achieve the 0°, 90°, 180°, and 270° driving signals. The phase shifter, e.g., included in the modulator that drives the transducer, provides the phase shifted excitation signals applied to each successive element of the transducer.

In the second approach, which is preferred because it simplifies the electronic package required and because it facilitates use of a simpler, double-sided electrode pattern, the piezoelectric plastic material must be locally polarized in a specific direction, depending upon the desired phase of the electrode at that location. A polarity reversal provides a 180° phase shift, eliminating the need for 180° and 270° electronic signals. Thus, the zones of the substrate designated as 0 and 90° would be connected to the signal source with the poles of the elements in one direction, while zones for elements designated to provide a relative phase shift of 180° and 270° would be connected with the poles of the elements in the opposite direction. Elements producing ultrasonic waves with a relative phase relationship of 0° and 180° would comprise one group, and elements producing ultrasonic waves with a relative phase relationship of 90° and 270° would comprise a second group. Connecting the poles of the different groups in local regions in opposite directions is achieved by applying electric fields of opposite polarity in those areas during manufacture of the conformal array transducer. The final element wiring pattern required to actually energize the conformal array transducer when it is employed for monitoring flow and/or velocity of fluid through the vessel would preclude applying electric fields in opposite polarity. Accordingly, the required polarity relationship would have to be performed using either temporary electrodes or by providing temporary breaks in the actual electrode pattern employed in the final conformal array transducer.

In the preferred embodiment, to achieve a desired frequency of operation, it is contemplated that the electrode mass would be increased to a point well beyond that required for making electrical connections. This added mass would act together with the piezoelectric plastic material to form a physically resonant system at a desired frequency. In this manner, a relatively thinner and more flexible piezoelectric plastic material can be used for the substrate comprising band 172. Use of mass loading in this manner is well known to those of ordinary skill in the art of transducer design, at least in connection with producing large, single element, piston transducers.

Figure 14:
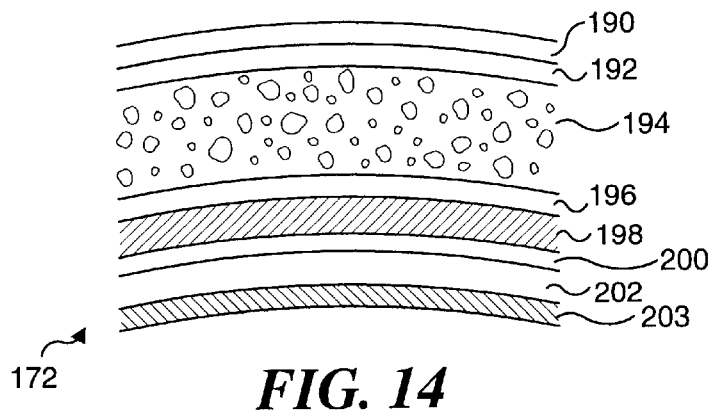
FIG. 14 is an enlarged, partial transverse cross-sectional view of the layers comprising the conformal transducer array mounted on a carrier band that is disposed around a vessel wall.

The conformal array transducers can be formed on band 172, but alternatively, can be included within the structure of an artificial cardiac valve, as discussed below. FIG. 14 illustrates a portion of a cross-sectional view of the conformal array transducer fabricated on band 172. The entire transducer assembly is covered with an outer coating 190 made from a biocompatible material that serves as a barrier to protect the conformal array transducer from bodily fluids. Below the outer coating is an RF shield 192, comprising electrically conductive flexible material or a thin foil that provides RF shielding to minimize EMI radiated from the conformal array transducer assembly. An acoustic backing 194 comprising a conventional, or a syntactic foam, i.e., a polymer loaded with hollow microspheres, such as is well known to those of ordinary skill in the art, serves both for acoustic isolation and dampening and to minimize capacitive loading. The acoustic backing has a relatively low dielectric constant, thereby minimizing capacitive loading between the electrodes and surrounding tissue. Acoustic backing 194 thus insulates the transducer elements from the surrounding fluid and tissue in a capacitive sense, and also in an acoustic sense. The next layer radially closer to the longitudinal center of the vessel comprises a rear electrode 196. A front electrode 200 is spaced apart from the rear electrode by a piezoelectric plastic layer 198. As noted above, in the preferred embodiment illustrated in FIGS. 11–13, piezoelectric plastic layer 198 comprises band 172. Piezoelectric layer 198 (or band 172) has a relatively low dielectric constant, e.g., from about six to eight) compared to tissue (approximately 80).

Rear electrode 196 and front electrode 200 preferably comprise multi-layer structures (although separate layers are not shown). For example, the electrodes will include a metallic layer, such as titanium, that bonds well to the piezoelectric plastic material, followed by a highly conductive layer, such as copper, followed by an oxidation resistant layer, such as gold. Such multi-layer systems are well known in the field of electronic interconnects and are ideally suited for use as electrodes in the conformal array transducer. Preferably, front electrode 200 is the "common electrode" for the transducer elements and serves as an RF shield. A front coating 202 serves as an acoustic coupling between the conformal array transducer and the vessel about which it is applied. In addition, the front coating layer serves as a biocompatible layer, providing a barrier to fluid ingress into the conformal array transducer. The transducer assembly comprising each of the layers disclosed above is wrapped around and in contact with a vessel wall 203 as shown in FIG. 14.

Figure 15:
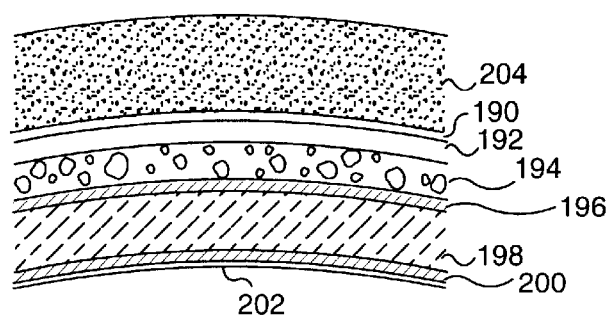
FIG. 15 is an enlarged, partial transverse cross-sectional view of the layers comprising the conformal transducer array disposed within a artificial cardiac valve wall or within a band that is coupled around a cardiac vessel to monitor blood flow therethrough.

Referring now to FIG. 15, an embodiment of the conformal transducer array fabricated as an integral component of a wall of an artificial cardiac valve is illustrated (only a portion of a cross section showing the plurality of layers comprising the device is illustrated). An artificial cardiac valve material 204 provides the primary structure for the valve support and is adapted to be sutured into a patient's heart, replacing a natural cardiac valve, as explained below. Typically, the valve support material is characterized by a moderate attenuation of ultrasonic signals. Below support material 204 is disposed outer coating 190 comprising a biocompatible material that protects the transducer elements, and other components of the transducer system from bodily fluids. Below outer coating 190 is disposed RF shield 192, to minimize transmission of EMI outside the patient's body. Acoustic backing 194 is disposed between RF shield 192 and rear electrode 196, and as described above, is a relatively lossy material. Piezoelectric material 198 couples rear electrode 196 and front electrode 200 and comprises one of the flexible piezoelectric plastics noted above. Front coating 202 is applied to the inner surface of the transducer assembly and is selected for its biocompatibility, to withstand exposure to bodily fluids.

In both the conformal array transducer assembly provided in band 172 (as shown in FIGS. 11–13) and the transducer assembly included within the structure of the artificial cardiac valve support, as illustrated in FIG. 15, it is contemplated that adhesive layers (not shown) may be used between the various layers. However, certain layers such as front and rear electrodes 200 and 196 will likely need not be adhesively coupled to the piezoelectric material if photolithographically formed on the material. Other layers may not require an adhesive to couple to adjacent layers, e.g., if formed of a thermoset material that self bonds to an adjacent layer when set.

Figure 16:
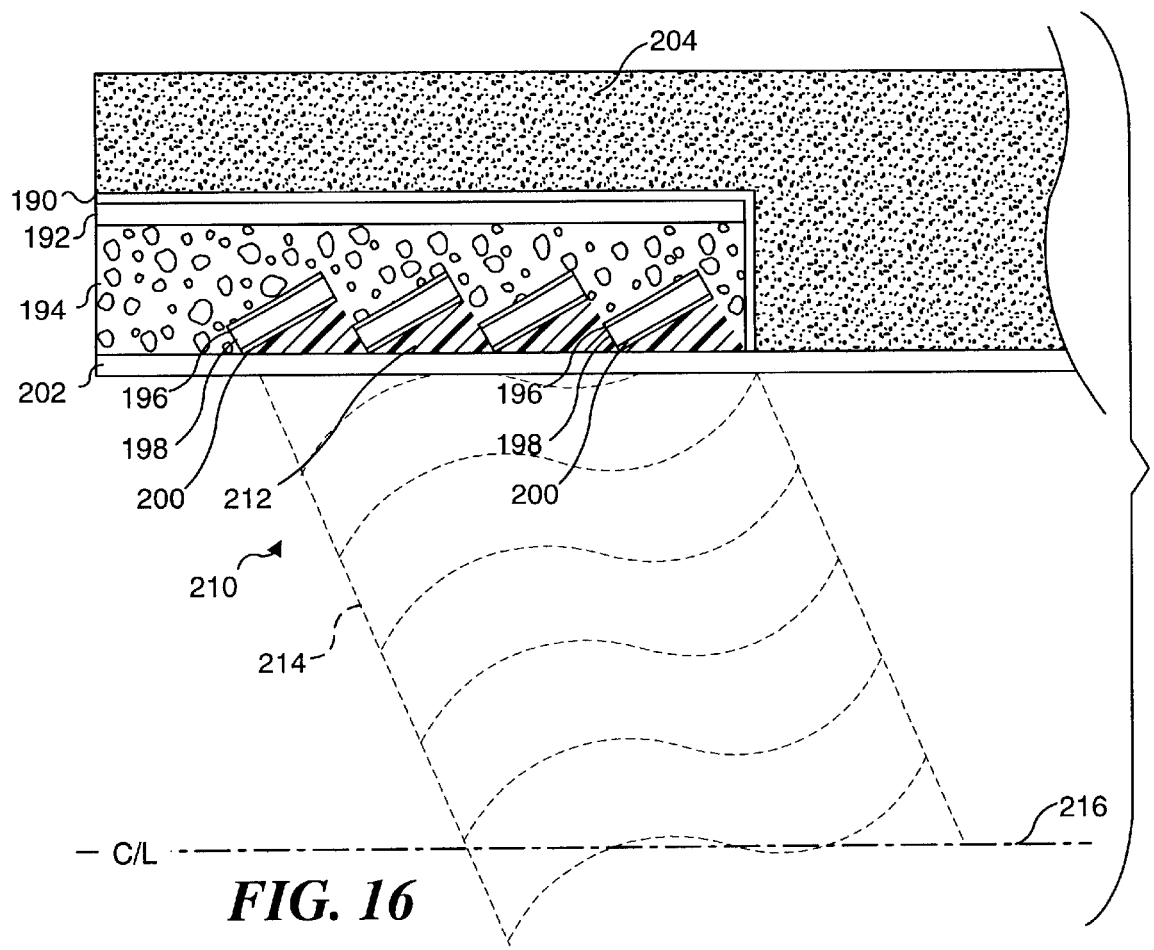
FIG. 16 is an enlarged, partial cross-sectional side view of a tilted-element transducer array disposed within a wall of an artificial cardiac valve or within a band that is coupled around a cardiac vessel to monitor blood flow therethrough.

As noted above, one of the advantages of the conformal array transducer is its relatively low profile. In some cases, an artificial cardiac valve or a cuff for use around a cardiac blood vessel to monitor flow therethrough may accommodate a relatively thicker profile transducer assembly within it. An embodiment of a tilted element transducer 210 is illustrated in FIG. 16. Each element comprising tilted element transducer 210 includes rear electrode 196 and front electrode 200 disposed on opposite sides of piezoelectric material 198. Conventional prior art transducers for producing an ultrasonic waves use a single such element that has a substantially greater width that is too great for inclusion in the support of an artificial cardiac valve or a cuff to monitor blood flow through a cardiac vessel. In contrast, tilted element transducer 210 includes a plurality of elements like those shown in FIG. 16 that minimize the radial height (or thickness) of the transducer.

The tilted element transducer is built into the support for the artificial cardiac valve or cuff, generally as shown in FIG. 16 and includes coating 190, which again serves the function of providing a biocompatible layer to protect the interior portion of the device and the transducer components contained therein from exposure to bodily fluids. Inside outer coating 190 is support material 204, which comprises the overall structure of the device. RF shield 192 extends over the portion of the device in which tilted element transducer array 210 is disposed within the protection provided by coating 190. Below RF shield 192 is disposed acoustic backing 194.

An acoustic filler material 212 is disposed between front electrode 198 and front coating 202, on the interior surface of the device, and is used to fill in the cavities in front of the transducer elements. The acoustic filler material is characterized by a relatively low ultrasonic attenuation, so that it readily conveys the ultrasonic waves produced by the elements into the chamber of the heart adjacent to an artificial cardiac valve provided with ultrasonic transducers or into the interior of a blood vessel about which a cuff including the transducers is secured. In order to minimize reverberations of the ultrasonic waves in this acoustic filler material, its acoustic impedance, which is equal to sound velocity times density, is approximately equal to that of the fluid in the vessel or heart chamber. The velocity of sound in the acoustic filler material should also be close to that of the blood flowing through the chamber (or vessel if used in a cuff) so that the sound beam is not significantly deflected by the acoustic filler material. Alternatively, an acoustic filler material having a relatively low sound velocity compared to the fluid or wall may be used. In this case, the acoustic filler material acts as an acoustic lens that deflects the sound being produced by the tilted transducer elements, for example, materials such as silicones or fluorosilicones, typically having sound velocities of about 1000 meters per second (compared to a sound velocity of approximately 1540 meters per second for blood), may be used. Low velocity lenses are generally well known in the art of ultrasonic transducers. The benefit of using a low velocity acoustic filler material is that the tilted transducer elements can be tilted about 30% less than would be required otherwise. As a result, the overall height of the tilted element transducer portion of the artificial cardiac valve or cuff can be made about 30% thinner than would be possible without the low velocity acoustic filler material. In combination, the plurality of tilted elements produce an ultrasonic wave 214 that propagates at an angle relative to the longitudinal axis of the device, which is represented by a center line 216 in FIG. 16.

Figure 17A:
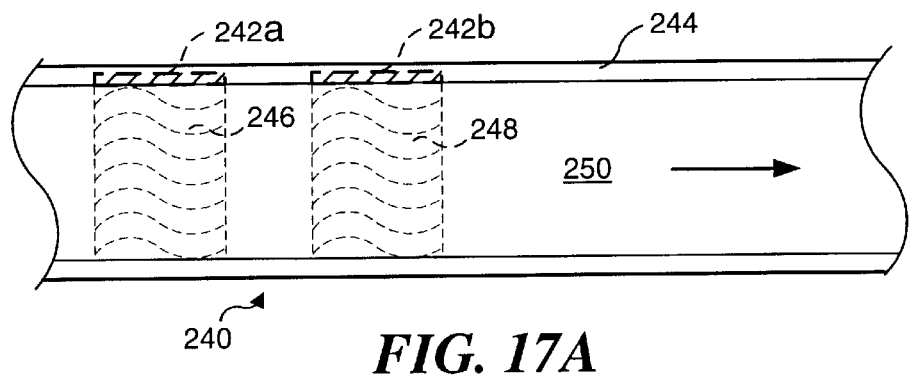
FIG. 17A is a cross-sectional side view of a portion of a band or cuff in which are disposed transversely oriented transducers for monitoring flow using correlation measurements.
Figure 17B:
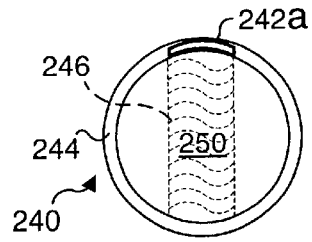
FIG. 17B is a transverse, cross-sectional view of the band cuff shown in FIG. 17A.

In FIGS. 17A and 17B, an alternative approach for monitoring the velocity of a fluid through an interior 250 of a cuff 240 is illustrated. In this embodiment, a pair of ultrasonic transducers 242a and 242b are mounted in relatively close proximity within a wall 244 of cuff 240. Alternatively, the ultrasonic transducers may be disposed externally in contact with the outer surface of a cuff that is wrapped around a cardiac vessel. Ultrasonic transducers 242a and 242b each produce a pulse and receive the echo back from fluid flowing through interior 250 of the cardiac vessel, the echoes being scattered from the fluid flowing therein. In this embodiment, the signal received from transducer 242a in response to the echo is correlated with the similar signal from ultrasonic transducer 242b, resulting in a time delay estimate. The velocity of the fluid is then computed by dividing a distance between the center of transducer 242a and the center of transducer 242b by the time delay that was determined from the correlation analysis.

Unlike a Doppler system, the echoes in a correlation type transducer system like that shown in FIGS. 17A and 17B are not frequency shifted. Instead, the velocity signal is extracted by correlating the echo amplitude versus time signals for a pair of range bins. The velocity versus time is independently determined for each range bin, resulting in a time-dependent velocity profile across the diameter of the cardiac vessel.

Figure 18:
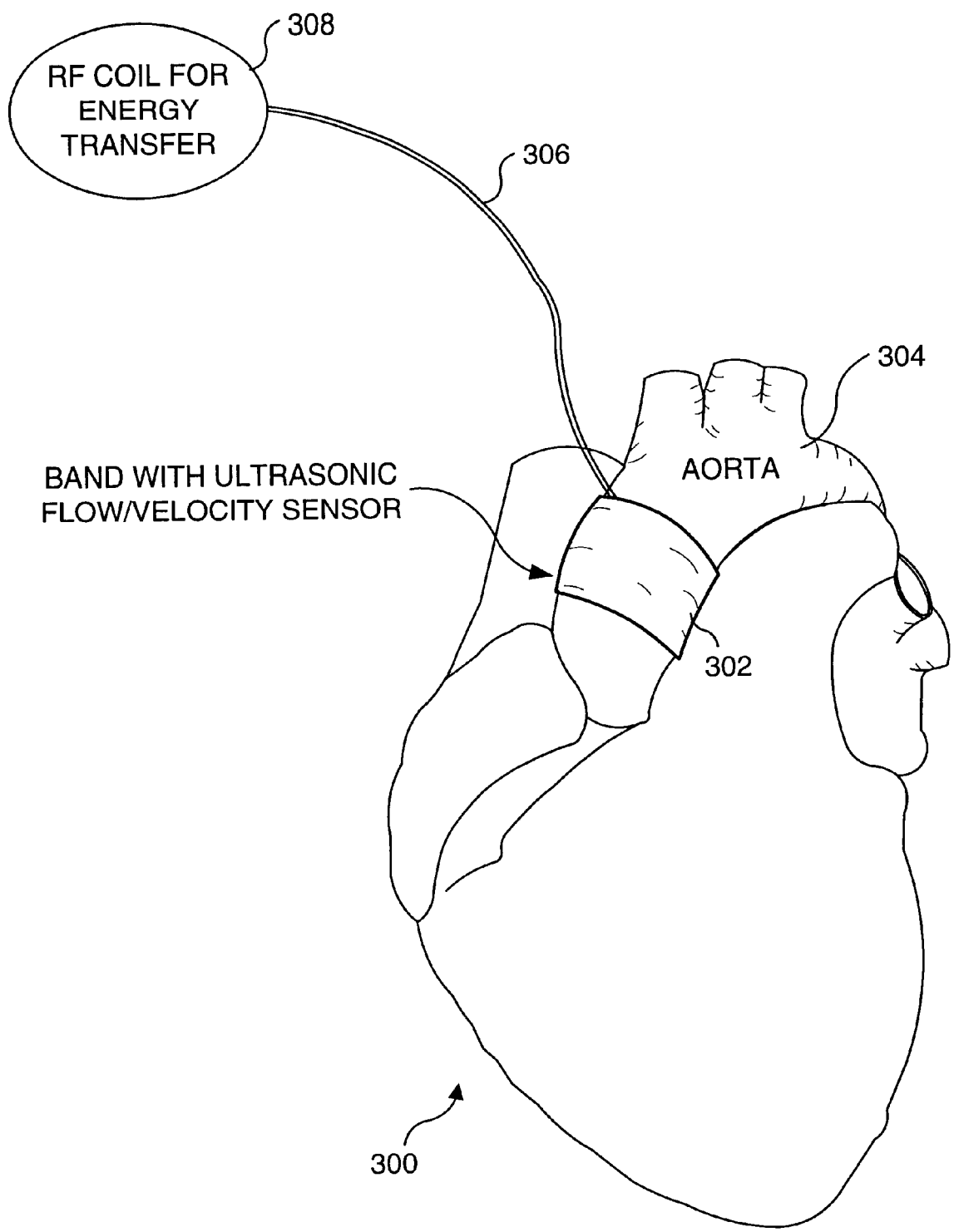
FIG. 18 is a ventral view of a human heart and portions of the adjacent vessels, showing the present invention applied to the aorta for monitoring the flow of blood to determine the condition of the aorta valve.

In FIG. 18, a human heart 300 is shown and has a cuff or band 302 wrapped around an aorta 304 for purposes of monitoring blood flow and/or blood velocity through the aorta, and thus, the condition of the aortic valve. The ultrasonic transducers within band 302 are coupled through leads 306 to an RF coil 308 that is used to supply electrical energy to the ultrasonic transducers, as explained above. Signals indicative of the flow of blood through aorta 304 and indicative of the condition of the aorta valve are transmitted from the ultrasonic transducers to an external receiver, also as described above.

It is contemplated that band 302 will be fabricated and configured as described above. Particularly suitable for use in monitoring blood flow and/or velocity through a cardiac vessel such as aorta 304 are the ultrasonic transducers comprising conformal arrays 174a and 174b, as shown in FIGS. 11–13.

As noted above, if it is necessary to temporarily cut the cardiac vessel about which band 302 is applied, the band need not be cut, but instead, can simply be slipped over the excised end of the vessel. Thus, if the band is to be used for monitoring the condition of an artificial valve in the aorta that was just replaced, and the procedure employed to install the artificial valve required cutting the aorta, the band can be installed at that time. When there is no longer any need to monitor the condition of the cardiac valve, the surgeon can simply cut through the band to remove it from the cardiac vessel around which it was applied. However, as was noted above, if the vessel is not cut, it is also possible to split the conformal arrays by cutting along cut line 175 (FIG. 13), thereby enabling the band to be wrapped around the intact cardiac vessel. The ends of band 302 are preferably then sutured together and may be tacked to the vessel wall with sutures to hold the band in place. Alternatively, a biocompatible adhesive can be applied to hold the band in position on the vessel.

The ultrasonic transducers included within band 302 monitor blood flow and/or velocity through aorta 304, which serves as an indication of the condition of either a natural of an artificial aorta valve (neither shown) in heart 300. For example, if the aorta valve is leaking, the flow of blood through the leaking valve when it is nominally closed will be evident from the flow and/or velocity of the blood through the cardiac vessel being monitored. If a cardiac valve is operating correctly, when the valve is fully closed, the flow of blood and its velocity through the cardiac vessel associated with the valve should be nearly zero. Failure of a cardiac valve to fully open will be evident if a maximum flow of blood or a maximum velocity of blood is monitored that is substantially less than would be expected through a fully open valve. Fluttering of valve components due to the malfunction of the valve should be evident as oscillations in the blood flow and/or velocity of blood flowing through the cardiac vessel that is being monitored by the ultrasonic transducers included within band 302. Accordingly, it will be apparent that the operational condition of a cardiac valve and any incipient failure or malfunction of the valve is determinable by monitoring the flow of blood and/or its velocity through the vessel coupled to the valve.

While the illustrated exemplary application of the present invention in FIG. 18 shows band 302 coupled around aorta 304 to monitor the condition of the aorta valve in aorta 304, it will be apparent that the band can also be placed around one of the other vessels coupled in fluid communication with heart 300 to monitor the condition of a cardiac valve adjacent to the vessel that controls the flow of blood either into or out of heart 300. The same functionality is achieved, regardless of the specific cardiac vessel or cardiac valve being monitored. Furthermore, by coupling the signal produced by the ultrasonic transducers to a receiver coil (not shown) that is coupled to a remote monitoring site via a radio link, the patient may continue to be ambulatory, and the condition of the cardiac valve can be monitored on a continuous or periodic basis by medical personnel, with minimal disruption of the patient's life.

Figure 19:
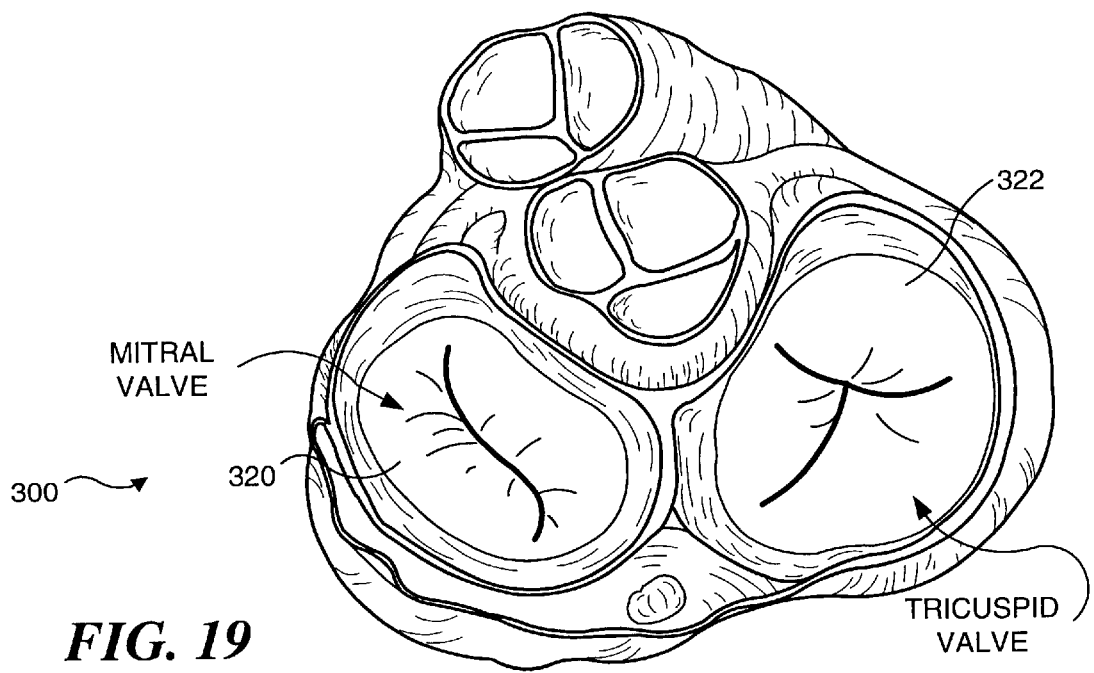
FIG. 19 is a sectional view of a human heart from above, after the atria and arterial trunks have been removed to more clearly show the bicuspid (mitral) and tricuspid valves.
Figure 21:
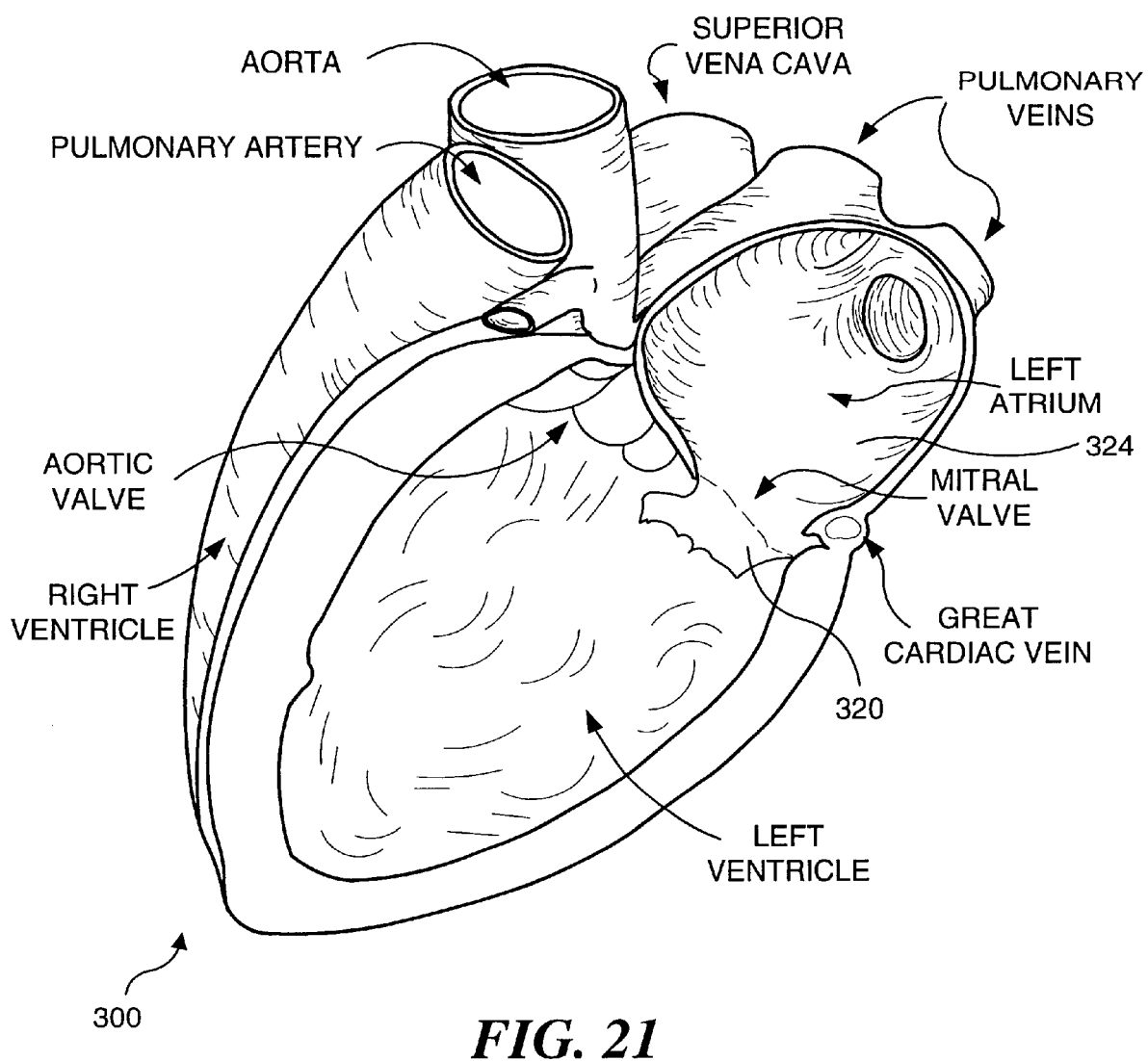
FIG. 21 is a cross-sectional, simplified view of the right and left ventricles of a human heart, showing the disposition of the mitral valve.

Although band 302 is capable of monitoring blood flow through the aortic and pulmonary valves, it is not possible to accurately monitor blood flow through the tricuspid and mitral valves by simply monitoring flow through the external vessels of the heart. FIGS. 19 and 21 show the location of various components of heart 300, including a mitral valve 320, which is below left auricle or atrium 324 and opens to enable blood to flow into the left ventricle, during diastole, while a tricuspid valve 322 (FIG. 19) opens to enable blood to flow into the right ventricle.

It is further contemplated that band 302 can be positioned around other tubular structures within a patient's body to monitor the flow (or velocity) of a fluid through the tube to determine a condition within the patient's body. For example, the band can be installed around a bile duct (not shown) to monitor the flow of liver bile through the duct to evaluate a condition of the liver (or the duct). It can also be installed around the urinary tract in a patient to monitor the flow of urine, to evaluate the condition of the bladder or other related conditions in the patient's body.

Figure 20:
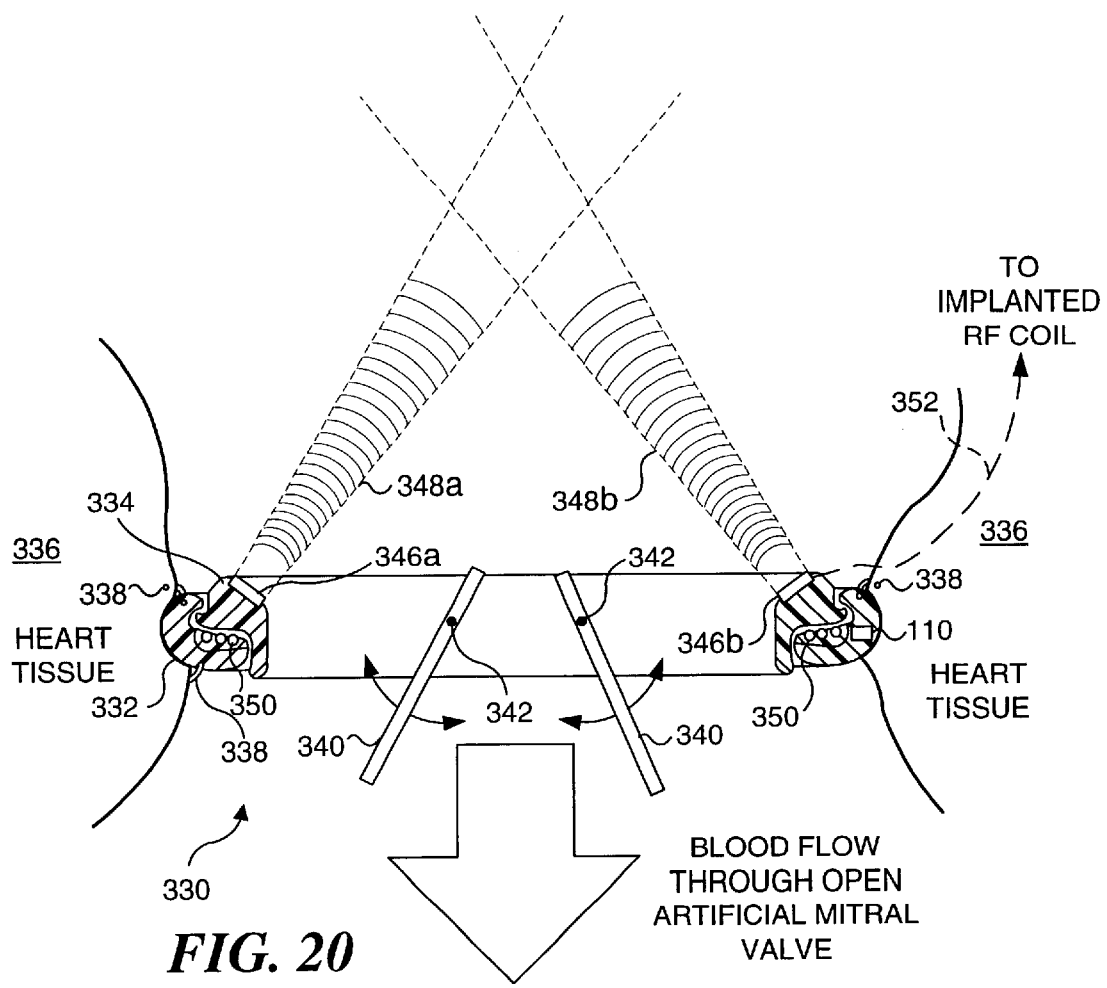
FIG. 20 is a cross-sectional view through one embodiment of an artificial cardiac valve that includes flow transducers to monitor flow through the valve and thus, to determine the condition of the valve.

As shown in FIG. 20, an artificial cardiac valve 330 provided with integral flow sensing can replace a diseased mitral valve (or tricuspid valve) in a patient's heart. Artificial cardiac valve 330 includes a generally annular sewing ring 332 that is fabricated from a woven material such as DACRON™ and is sutured to surrounding heart tissue 336 with sutures 338. An annular valve body 334 is preferably fabricated from a metal such as titanium or from vitreous carbon and servers to support pivot pins 342 about which generally semi-circular leaflet valve plates 340 pivot between an open position (as shown if FIG. 20) and a closed position in which the leaflet valve plates are pivot to block blood flow through the artificial cardiac valve during systole. The leaflet valve plates are preferably fabricated from vitreous carbon, but may instead comprise human or animal (e.g., porcine) tissue. It should be noted that the present invention can also be used with other types of cardiac valves (not shown), including those provided with a valve element using either only one leaflet valve plate, more than two leaflet valve plates, or a ball in a cage. It is important to note that only the supporting structure for an artificial cardiac valve must be modified to monitor fluid flow through an artificial cardiac valve; it is not necessary to modify the valve element used. Accordingly, almost any type of valve element can be employed with the present invention.

In the exemplary embodiment for sensing flow through artificial cardiac valve 330 as shown in FIG. 20, a pair of ultrasonic flow transducers 346a and 346b are employed, generally consistent with any of the ultrasonic flow transducers described above. An integral RF coupling coil 350 made of a plurality of turns of insulated wire conductor is disposed in sewing ring 332, with the coils extending around the annular shape of the sewing ring and is thus part of the implanted artificial cardiac valve. Alternatively, the ultrasonic flow transducer may be coupled to a separate RF coil (not shown) that is implanted under a dermal layer on the patient's body by a lead 352, thereby enabling the RF coil to be closer to the surface of the patient's body to improve the effectiveness for coupling energy into the ultrasonic flow transducers and for transmitting the flow data signals produced thereby to the external monitoring receiver, as explained above.

If multiple ultrasonic flow sensors are used, as shown in the Figure, it will be advantageous to include electronics assembly 110 in sewing ring 332. As previously noted, the electronics assembly can include any of the circuits described above in connection with FIGS. 1–6, and may employ the multiplexers in those circuits to enable the flow signals produced by the transducers to be separately provided to the external monitoring receiver in sequence, and to provide the power to energize the ultrasonic flow transducers. It is contemplated that it will be preferable to employ a range-gated pulsed Doppler technique in which a frequency shift from one pulse-echo sequence to the next is applied with a resent time window corresponding to the range of interest. Multiple time windows may be acquired and processed from each pulse, which is referred to as a multi-gate Doppler process in the field of ultra sound. Using the multiple gates, a velocity profile for blood flowing through the artificial cardiac valve can be determined.

A single ultrasonic flow transducer element can only acquire one component of the flow vector at a given spatial location. To more fully quantify the flow field through the valve, it may be necessary to use at least two ultrasonic flow transducers, as shown in the exemplary illustration. In FIG. 20, ultrasonic flow transducer 346a produces a beam 348a of ultrasonic pulses, while ultrasonic flow transducer 346b produces a beam 348b, from an opposite side of the support for the valve. These two beams are directed upstream (into the left atrium) in this example and intersect above the artificial cardiac valve.

Multiple ultrasonic flow transducers on an artificial cardiac valve can be used in several different ways. For example, transmitting, receiving, and processing ultrasonic signals from a first ultrasonic flow transducer can provide a flow vector component measurement for each range gate along the beam produced by that ultrasonic flow sensor. However, repeating this process with a second ultrasonic flow transducer provides additional vector components along the beam produced by the second ultrasonic flow transducer. It is also contemplated that additional ultrasonic flow transducers could be employed in the same manner to more completely sample the flow field. Alternately (or in addition), the ultrasonic beam transmitted from one ultrasonic flow transducer can be received by the other ultrasonic flow transducer, where, as shown, the ultrasonic beams intersect in the blood flow field. Processing the resulting signals produced by the flow transducers provides a flow vector component measurement along a line bisecting the angle between the two intersecting ultrasonic beams.

It will likely be preferable to position the ultrasonic flow transducers so that the ultrasonic beams are not affected by the moving valve element(s), to minimize any effect of the leaflet plate(s) or ball moving when the valve is actuated. The flow in the valve is relatively complex, making measure of blood flow within the valve difficult. For a similar reason, it is preferable to direct the ultrasonic flow transducers into the cardiac chamber disposed upstream of the artificial cardiac valve. While the ultrasonic flow transducers could be aligned and their signals range-gated to sense flow in the cardiac chamber downstream of the artificial cardiac valve, the flow pattern downstream thereof may broaden out or curve, and it would be difficult to ensure that the sensing zone is in the optimal location within the flow field. Furthermore, the ultrasound beams can be reflected from a leaflet valve plate can reflect an ultrasound beam causing the flow sensed to be in an adjacent vessel as the leaflet valve plate moves in and out of the ultrasound beam. Accordingly, in the preferred embodiment, the ultrasound flow transducers are positioned to direct and gate ultrasound pulses in beams directed just upstream of the artificial cardiac valve.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A band adapted to be applied externally around a cardiac vessel in a vicinity of a cardiac valve to monitor a condition of the cardiac valve that controls blood flow through the cardiac vessel in a patient's body, comprising:
   (a) a biocompatible material that is sufficiently elastomeric to be wrapped around said cardiac vessel, forming a cuff;
   (b) a first transducer disposed within the wall of the cuff, said first transducer producing a signal indicative of a parameter of the blood flowing through the cardiac vessel, and thus, indicative of a condition of the cardiac valve; and
   (c) a coil coupled to the first transducer for conveying the signal to a point external to the patient's body, for use in evaluating a condition of the cardiac valve, as a function of the parameter of the blood flowing through the cardiac vessel.

2. The band of claim 1, wherein said first transducer includes a plurality of elements formed on a piezoelectric substrate, which when excited by a radio frequency signal, emit ultrasonic waves that propagate into the cardiac vessel, said ultrasonic waves being affected by the blood flowing through the cardiac vessel, further comprising a receiver of the ultrasonic waves that produces the signal indicative of the parameter, said receiver being coupled to the coil so that the signal produced by the receiver is conveyed outside the patient's body.

3. The band of claim 2, wherein the parameter is one of a velocity and a flow of the blood through the cardiac vessel, said signal indicative of the parameter being determined as a function of the blood's effect on the ultrasonic waves within the cardiac vessel.

4. The band of claim 2, wherein the receiver comprises a second transducer that includes a plurality of elements formed on a piezoelectric substrate, said second transducer being disposed within the wall of the cuff and responding to the effect of the blood in the cardiac vessel on the ultrasonic waves to produce the signal indicative of the parameter.

5. The band of claim 4, wherein the first transducer and the second transducer are disposed on opposite sides of the cuff, so that the ultrasonic waves pass through the cardiac vessel when traveling from the first transducer to the second transducer, said signal produced by the second transducer providing an indication of a transit time of the ultrasonic waves through the cardiac vessel.

6. The band of claim 5, wherein the plurality of elements comprising the first transducer and the second transducer are sufficiently flexible to conform to a curved shape of an exterior surface of a cardiac vessel.

7. The band of claim 5, wherein the plurality of elements comprising the first transducer are divided into a first portion and a second portion, elements comprising the first portion being interdigitally dispersed among elements comprising the second portion and adapted to couple to the radio frequency signal in one polarity, the elements comprising said second portion being adapted to couple to the radio frequency signal with an opposite polarity, so that the ultrasonic waves produced by the elements comprising the second portion are phase shifted by about 180° relative to the ultrasonic waves produced by the elements comprising the first portion.

8. The band of claim 5, further comprising a phase shifter, wherein the elements comprising the first transducer are divided into four portions arranged in an ordered array in which each successive element is from a different one of the four portions, taken in order, the radio frequency signal being applied to the phase shifter, and a phase shifted signal produced by the phase shifter being applied to at least two of each successive four elements to provide about a 90° phase difference between the ultrasonic waves emitted by successive elements, so that the ultrasonic waves that are emitted by the first transducer in one direction are substantially canceled due to a destructive interference.

9. The band of claim 4, wherein the first transducer and the second transducer are spaced apart from each other along a side of the cuff, further comprising a reflector disposed on an opposite side of the cuff from the first transducer and generally opposite a point between the first transducer and the second transducer, so that the ultrasonic waves from the first transducer pass through the cardiac vessel and are reflected back toward the second transducer by the reflector.

10. The band of claim 4, wherein the first transducer and the second transducer alternately function as an emitter and as a receiver of the ultrasonic waves during successive time intervals, said radio frequency signal being coupled to the plurality of elements comprising the second transducer when it functions as the emitter, while the plurality of elements comprising the first transducer are then coupled to the coil and produce the signal indicative of the parameter in response to the ultrasonic waves affected by the blood in the cardiac vessel.

11. The band of claim 10, further comprising a multiplexer that is used for alternately coupling the first and the second transducers to the radio frequency signal and to the coil.

12. The band of claim 2, wherein the frequency of the radio frequency signal is controlled to determine a beam angle along which the ultrasonic waves are emitted by the first transducer.

13. The band of claim 2, wherein the coil is adapted to couple to a source of energy that is external to the patient's body, to provide electrical power for energizing electrical components of the band.

14. The band of claim 13, wherein the coil is adapted to electromagnetically couple to an external coil that is connected to the source of energy.

15. The band of claim 2, wherein the receiver comprises the first transducer, said radio frequency signal being applied to the plurality of elements as a pulse, causing the plurality of ultrasonic waves to be emitted as a pulse, said plurality of elements comprising the first transducer then receiving an echo of the pulse of the ultrasonic waves that is reflected from the blood to determine the parameter based on a Doppler effect.

16. The band of claim 1, wherein the coil is disposed within the wall of the cuff.

17. The band of claim 1, wherein the coil comprises an insulated wire formed in a plurality of loops.

18. The band of claim 1, wherein the coil is adapted to be implanted under a dermal layer in the patient's body, separate from the band and electrically coupled thereto.

19. A system for monitoring a parameter indicative of a condition of a cardiac valve, said system comprising:

(a) a carrier band that is adapted to couple about a cardiac vessel through which blood flows either to or from the cardiac valve, so that the carrier band is in close proximity to at least one side of the cardiac vessel;

(b) a first transducer having at least one conformal element disposed on the carrier band, said at least one conformal element being sufficiently flexible and shaped so that it is adapted to curve about the cardiac vessel, conforming to its shape, said first transducer being adapted to couple to a radio frequency signal and producing ultrasonic waves when excited by the radio frequency signal, said ultrasonic waves being emitted from said at least one conformal element and being directed into an interior of the cardiac vessel; and (c) a receiver disposed to receive the ultrasonic waves after they have propagated at least partially through the cardiac vessel, said receiver producing a signal indicative of an effect on the ultrasonic waves due to the blood in the cardiac vessel and thus, indicative of a parameter relating to a flow of the blood through the cardiac vessel and of a condition of the cardiac valve.

20. The system of claim 19, wherein the ultrasonic waves are emitted as a pulse, the first transducer alternately comprising an emitter of the pulse of the ultrasonic waves, and then comprising the receiver, said pulse of ultrasonic waves being reflected from the blood in the cardiac vessel back toward the first transducer.

21. The system of claim 19, wherein the carrier band is formed of a material adapted to be disposed within a patient's body, said system being used to monitor the flow of the blood through the cardiac vessel to determine whether the cardiac valve is functioning properly.

22. The system of claim 21, further comprising a second transducer having at least one conformal element on the carrier band, said at least one conformal element being sufficiently flexible and shaped so that it is adapted to curve about the cardiac vessel, conforming to a shape of the cardiac vessel.

23. The system of claim 22, wherein said second transducer is adapted to couple to the radio frequency signal and produces ultrasonic waves when excited by the radio frequency signal, said first transducer and said second transducer alternately interchangeably functioning as the receiver and as an emitter of the ultrasonic waves during successive time intervals.

24. The system of claim 22, wherein the first transducer and the second transducer are disposed on opposite sides of the carrier band when it is fitted about the cardiac vessel, said second transducer comprising the receiver of the ultrasonic waves emitted by the first transducer, said parameter being determined as a function of a transit time for the ultrasonic waves to pass through the cardiac vessel.

25. The system of claim 22, wherein said at least one conformal element of each of the first transducer and the second transducer are shaped like segments of a sine wave having a period substantially equal to a circumference of the cardiac vessel.

26. The system of claim 25, wherein an amplitude of the sine wave having segments relating to the shape of said at least one conformal element of each of the first and the second transducers substantially determines a beam angle of the ultrasonic waves.

27. The system of claim 22, wherein the carrier band comprises a substrate of a piezoelectric material on which a plurality of electrodes are formed to define conformal elements of the first and the second transducers.

28. The system of claim 27, wherein the piezoelectric material is uniformly polarized, every fourth electrode of the plurality of electrodes being coupled together.

29. The system of claim 27, wherein the piezoelectric material is zone polarized, every other electrode that comprises the plurality of electrodes being coupled together.

30. The system of claim 27, wherein the carrier band further comprises an acoustic backing layer that encompasses the plurality of electrodes formed on the piezoelectric material.

31. The system of claim 27, wherein the carrier band further comprises a radio frequency shield encompassing the plurality of electrodes formed on the piezoelectric material.

32. The system of claim 19, wherein the ultrasonic waves emitted by successive elements of the first transducer are 90° out of phase, so that the ultrasonic waves emitted in one direction are canceled due to a destructive interference.

33. The system of claim 19, further comprising a coil adapted to receive power from an external source and to provide an electrical current that is used for energizing components of the system.

34. The system of claim 33, wherein the coil is disposed within a wall of the carrier band.

35. The system of claim 33, wherein the coil is disposed on the carrier band.

36. The system of claim 33, further comprising a power supply, and a multiplexer, both being adapted to be internally disposed within the patient's body, said multiplexer alternately coupling the coil to the receiver and then to the power supply, so that power from the external source is supplied to the power supply when the coil is coupled to the power supplied by the multiplexer, and the signal produced by the receiver is supplied to the coil when the coil is coupled to the receiver.

37. The system of claim 19, wherein opposite ends of the carrier band are adapted to be joined after the carrier band is wrapped around the cardiac vessel.

38. The system of claim 19, wherein the parameter comprises at least one of a volumetric flow and a velocity of blood flowing through the cardiac vessel and the cardiac valve, any defects in the cardiac valve being evident in the parameter.

39. A method for remotely determining a condition of a cardiac valve within a patient's body, for an extended period of time, comprising the steps of:

(a) providing a first transducer that includes a plurality of elements for producing ultrasonic waves, carried on a band fitted about an exterior surface of the cardiac vessel, said plurality of elements being sufficiently flexible to conform to a curved shape of the cardiac vessel and being spaced apart along one side of the band;

(b) producing ultrasonic waves with the first transducer that are directed into the cardiac vessel, blood within the cardiac vessel affecting the ultrasonic waves;

(c) receiving the ultrasonic waves after they have been affected by the blood in the cardiac vessel, and producing a signal in response thereto that is indicative of a parameter related to the flow of the blood through the cardiac vessel;

(d) transmitting the signal to a point outside the patient's body; and (e) producing an indication of the parameter and thus of the condition of the cardiac valve, as a function of the signal.

40. The method of claim 39, wherein the first transducer emits a pulse of the ultrasonic waves, and then receives the ultrasonic waves reflected by the blood, a Doppler effect of the blood providing the indication of the parameter.

41. The method of claim 39, wherein a transit time of the ultrasonic waves through the cardiac vessel provides the indication of the parameter.

42. The method of claim 41, further comprising the steps of:

(a) providing a second transducer that includes a plurality of elements for producing ultrasonic waves, carried on the band, said plurality of elements being sufficiently flexible to conform to the curved shape of the wall and being spaced apart along a side of the band;

(b) receiving the ultrasonic waves with the second transducer; and (c) producing the signal in response to the ultrasonic waves that are received with the second transducer.

43. The method of claim 42, wherein the first and second transducers are disposed on a common side of the band, spaced apart from each other.

44. The method of claim 43, wherein the first and the second transducers each emit pulses of ultrasonic waves and each receive reflected pulses of the ultrasonic waves back from the blood, further comprising the step of correlating signals produced in response to the reflected pulses to determine the parameter.

45. The method of claim 43, further comprising the step of providing a reflector disposed on an opposite side of the band from that along which the first and the second transducers are disposed, wherein the second transducer receives the ultrasonic waves produced by the first transducer that have passed through the cardiac vessel, been reflected by the reflector, and passed back through the cardiac vessel.

46. The method of claim 44, wherein the second transducer is disposed on an opposite side of the band from the first transducer, said second transducer receiving the ultrasonic waves produced by the first transducer and producing the signal which varies as a function of a transit time through the cardiac vessel.

47. The method of claim 39, wherein the step of transmitting comprises the step of electromagnetically coupling the signal from a coil implanted within the patient's body to an external coil disposed outside the patient's body.

48. The method of claim 47, further comprising the step of electromagnetically coupling electrical energy from an external power source that is connected to the external coil to the coil implanted within the patient's body, to supply electrical power to at least the first transducer.

49. The method of claim 39, wherein the band is formed as a cylinder, further comprising the steps of cutting the band; wrapping the band around the cardiac vessel; and reconnecting ends of the band so that the band substantially encircles the cardiac vessel.

50. The method of claim 39, wherein the parameter comprises at least one of a volumetric flow of blood, and a velocity of blood flowing through the cardiac vessel.

51. The method of claim 39, further comprising the steps of cutting the cardiac vessel; slipping the band over the cut cardiac vessel, and reconnecting cut ends of the cardiac vessel.

52. The method of claim 39, further comprising the step of remotely monitoring the condition of the cardiac valve while a patient in which it is disposed is ambulatory.

53. An artificial cardiac valve that monitors blood flow therethrough to determine a condition of said cardiac valve after it is mounted in a patient's heart, comprising:

(a) a movable valve element, which in a first position, enables blood to flow in a desired direction through the artificial cardiac valve, but in a second position, blocks blood flow therethrough in an opposite direction;

(b) a generally annular support for the valve element;

(c) a flow transducer disposed within the support and oriented to monitor flow through the artificial cardiac valve within a portion of a chamber in a patient's heart after the artificial cardiac valve is mounted in said heart, said flow transducer producing a signal indicative of blood flow through the artificial cardiac valve during a cardiac cycle, said signal being indicative of a condition of the artificial cardiac valve and being adapted to couple through a radio link to an external monitoring site that is outside the patient's body to enable the condition of the artificial cardiac valve to be monitored at least from time to time;

(d) an additional flow transducer disposed within the support and oriented to monitor flow through the artificial cardiac valve within a different portion of said chamber, producing an additional signal that is adapted to couple with the external monitoring device through the radio link and which is further indicative of blood flow through the artificial cardiac valve, to better determine said blood flow and thereby, to better determine the condition of the artificial cardiac valve; and (e) a multiplexer that is coupled to the flow transducer and to the additional flow transducer, said multiplexer being adapted to selectively alternatively couple the flow transducer and the additional flow transducer to the radio link.

54. The artificial cardiac valve of claim 53, further comprising an antenna coil disposed within the support, said antenna coil being used to couple energy from an external source into the flow transducer to energize it and to transmit the signal produced by the flow transducer to the external monitoring device.

55. The artificial cardiac valve of claim 53, further comprising an implanted antenna coil that is adapted to be disposed within the patient's body, outside the patient's heart and apart from the flow transducer, but connected thereto, said implanted antenna coil being used to couple energy from an external source into the flow transducer to energize it and to transmit the signal produced by the flow transducer to the external monitoring device.

56. The artificial cardiac valve of claim 53, wherein the flow transducer produces range-gated pulsed Doppler ultrasonic pulses that are usable to determine blood flow velocity through the cardiac valve.

57. The artificial cardiac valve of claim 53, wherein the flow transducer and the additional flow transducer produce range gated ultrasonic pulses that are usable to determine blood flow along a line bisecting an angle between ultrasound beams produced by the flow transducer and the additional flow transducer, respectively.

58. The artificial cardiac valve of claim 57, wherein the flow transducer and the additional flow transducer are disposed on the support so that when the artificial cardiac valve is mounted in a patient's heart, the ultrasound beams are directed into a cardiac chamber disposed upstream from the artificial cardiac valve.

59. A method for monitoring blood flow through an artificial cardiac valve to determine a condition of said valve, comprising the steps of:
  (a) providing an artificial cardiac valve that includes at least one flow transducer disposed therein;
  (b) mounting the artificial cardiac valve within a patient's heart;
  (c) with said at least one flow transducer, producing ultrasonic pulses directed into a cardiac chamber adjacent to the artificial cardiac valve;
  (d) monitoring blood flow through the cardiac valve with said at least one flow transducer, producing a flow signal; and
  (e) transmitting the flow signal to an external receiver over a radio link, said flow signal indicating the blood flow through the artificial cardiac valve, enabling a condition of the artificial cardiac valve to be determined.

60. The method of claim 59, further comprising the steps of:
  (a) providing an antenna coil that is coupled to said at least one flow transducer;
  (b) transmitting the flow signal to the external receiver via the antenna coil; and
  (c) receiving electrical power to energize said at least one flow transducer from an external transmitter through the antenna coil.

61. The method of claim 60, wherein the antenna coil is disposed in the artificial cardiac valve.

62. The method of claim 61, further comprising the step of processing the ultrasonic pulses as a plurality of range-gated Doppler pulses.

63. The method of claim 62, further comprising the step of using the range-gated Doppler pulses to monitor blood flow velocity through the artificial cardiac valve, for use in determining a condition of the artificial cardiac valve.

64. A band adapted to be applied externally around a tubular passage in a patient's body to monitor a fluid flow through the tubular passage, comprising:
  (a) a biocompatible material that is sufficiently elastomeric to be wrapped around the tubular passage, forming a cuff;
  (b) a first transducer disposed within the wall of the cuff, said first transducer producing a signal indicative of a parameter of the fluid flowing through the tubular passage; and
  (c) a coil coupled to the first transducer for conveying the signal to a point external to the patient's body, for use in evaluating a condition of the patient's body, as a function of the parameter of the fluid flowing through the tubular passage.

* * * * *